US008637685B2

(12) United States Patent
Wiemer et al.

(10) Patent No.: US 8,637,685 B2
(45) Date of Patent: Jan. 28, 2014

(54) SCHWEINFURTHIN ANALOGUES

(75) Inventors: David F. Wiemer, Iowa City, IA (US); Jeffrey D. Neighbors, Iowa City, IA (US); Raymond J. Hohl, Iowa City, IA (US); Craig Kuder, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 390 days.

(21) Appl. No.: 13/001,509

(22) PCT Filed: Jun. 25, 2009

(86) PCT No.: PCT/US2009/048690
§ 371 (c)(1),
(2), (4) Date: Mar. 17, 2011

(87) PCT Pub. No.: WO2009/158516
PCT Pub. Date: Dec. 30, 2009

(65) Prior Publication Data
US 2011/0160297 A1    Jun. 30, 2011

Related U.S. Application Data

(60) Provisional application No. 61/076,500, filed on Jun. 27, 2008.

(51) Int. Cl.
C07D 311/82 (2006.01)
A61K 31/352 (2006.01)
(52) U.S. Cl.
USPC ..... 549/388; 546/282.7; 548/247; 548/311.4; 548/468; 549/220; 514/454
(58) Field of Classification Search
USPC .......................................... 549/388; 514/454
See application file for complete search history.

(56) References Cited

U.S. PATENT DOCUMENTS

| 7,358,377 B2 | 4/2008 | Wiemer et al. |
| 7,902,228 B2 | 3/2011 | Wiemer et al. |
| 2008/0015232 A1 | 1/2008 | Wiemer et al. |

FOREIGN PATENT DOCUMENTS

| WO | WO 2005/092878 A2 | 10/2005 |
| WO | WO 2010/127235 A1 | 11/2010 |

OTHER PUBLICATIONS

Neighbors et al, J. of Organic Chemistry, vol. 70, p. 925-931 (2003).*
Beutler et al., "Cytotoxic Geranyl Stilbenes from Macaranga schweinfurthii", *J. Nat. Prod.*, 61, 1509-1512 (1998).
Beutler et al., "Schweinfurthin D, a Cytotoxic Stilbene from Macaranga Schweinfurthii", Natural Product Letters, vol. 14(5), 399-404 (2000).
Dermer, "Another Anniversary for the War on Cancer", p. (1994). *BioTechnology, vol. 12*, 1.
Freshney, Culture of Animal Cells, a Manual of Basic Technique, Alan R. Liss, Inc., New York, 4 pp. (1983).
Gura, "Cancer Models, Systems for Identifying New Drugs are Often Faulty", *Science, vol. 278*, 2 pp. (1997).
Kodet et al., "Indole containing analogs of the natural schweinfurthins", 236th Acs National Meeting, Philadelphia, Pa, Medi 421, 1 p. (2008).
Kodet, "Studies on heteroaromatic schweinfurthin analogues", University of Iowa, Ph.D. Thesis, 1-275 (Dec. 2010).
MedicineNet.com, Definitiion of Cancer, 1 p. (Aug. 29, 2006).
Mente et al., "Total Synthesis of (R,R,R)-and (S,S,S)-schweinfurthin F: Differences of bioactivity in the enantiomeric series", *Bioorganic & Medicinal Chemistry Letters,17*, 911-915 (2007).
MSNBC News Services, "Mixed results on new cancer drug", 5 pp., Nov. 9, 2000.
Neighbors et al., "Synthesis of Nonracemic 3-Deoxyschweinfurthin B", *J. Org. Chem.,70*, 925-931 (2005).
Neighbors et al., "Synthesis and structure—activity studies of schweinfurthin B analogs: Evidence for the importance of a D-ring hydrogen bond donor in expression of differential cytotoxicity", *Bioorganic & Medicinal Chemistry, 14*, 1771-1784 (2006).
Neighbors et al., "Synthesis of the schweinfurthin hexahydroxanthene core through Shi epoxidation", *Tetrahedron Letters, 49*, 516-519 (2008).
Patent Cooperation Treaty, International Searching Authority, Search Report and Written Opinion for PCT/US2009/048690, 12 pages, Sep. 10, 2009.
Thoison et al., "Vedelianin, a Hexahydroxanthene Derivative Isolated from Macaranga Vedeliana", *Phytochemistry, vol. 31 (4)*, 1439-1442 (1992).
Treadwell et al., "A Cascade Cyclization Approach to Schweinfurthin B",*Organic Letters, vol. 4 (21)*, 3639-3642 (2002).
Yoder et al., "Antiproliferative Prenylated Stilbenes and Flavonoids from Macaranga alnifolia from the Madagascar Rainforest", *J. Nat. Prod., 70*, 342-346 (2007).

* cited by examiner

*Primary Examiner* — Bernard Dentz
(74) *Attorney, Agent, or Firm* — Viksnins Harris & Padys PLLP

(57) ABSTRACT

The invention provides fluorescent schweinfurthin analogs of formula (I) which are useful as probes and for the treatment of cancer and other diseases.

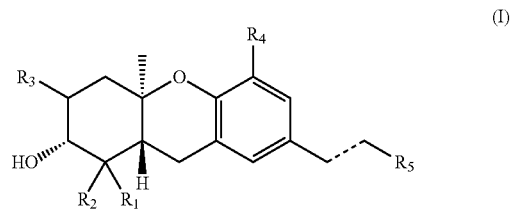

(I)

29 Claims, No Drawings

SCHWEINFURTHIN ANALOGUES

PRIORITY OF INVENTION

This application claims priority from U.S. Provisional Application No. 61/076,500, filed 27 Jun. 2008. The entire content of this provisional application is hereby incorporated herein by reference.

BACKGROUND OF THE INVENTION

The family of natural products known as the schweinfurthins includes four compounds isolated from the African plant *Macaranga schweinfurthii* Pax (see Beutler, J. A. et al., *J. Nat. Prod.* 1998, 61, 1509-1512; and Beutler, J. A., et al., *Nat. Prod. Lett.* 2000, 14, 349-404). Schweinfurthins A, B, and D display significant activity in the NCI's 60-cell line anticancer assay with mean $GI_{50}$'s<1 µM. Their biological activity has attracted interest because some CNS, renal, and breast cancer cell lines are among the types most sensitive to these compounds. Inspection of the spectrum of activity shows no correlation with any currently used agents and suggests that these compounds may be acting at a previously unrecognized target or through a novel mechanism.

The further development of schweinfurthins as cancer therapeutics would be accelerated by elucidating their mechanism of action. Currently there is a need for schweinfurthin analogs that can be used as probes for elucidating the mechanism of action of these unique anti-cancer agents.

SUMMARY OF THE INVENTION

Many schweinfurthin analogues are fluorescent under UV light. After treatment with 3-deoxy schweinfurthin B, SF-295 cells (human glioblastoma multiforme) were examined for potential UV fluorescence. Unfortunately, 3-deoxy schweinfurthin B failed to generate a significant fluorescent signal above autofluorescence of control cells.

Applicant has discovered a series of modified schweinfurthin analogs that possess beneficial fluorescent properties as well as significant anti-cancer activity. Accordingly, in one embodiment, the invention provides a compound of formula (I):

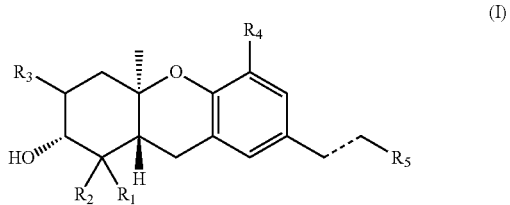

(I)

wherein:

$R_1$ and $R_2$ are each independently H, $(C_1-C_6)$alkyl, halo$(C_1-C_6)$alkyl or $(C_3-C_8)$cycloalkyl; or one of $R_1$ and $R_2$ is carboxy and the other is H, $(C_1-C_6)$alkyl, halo$(C_1-C_6)$alkyl or $(C_3-C_8)$cycloalkyl;

$R_3$ is H, $(C_1-C_{15})$alkyl, $(C_2-C_{15})$alkenyl, $(C_2-C_{15})$alkynyl, $(C_1-C_{15})$alkoxy, $(C_1-C_{15})$alkylthio, $(C_1-C_{15})$alkanoyl, $(C_1-C_{15})$alkoxycarbonyl, $(C_2-C_{15})$alkanoyloxy, hydroxy, mercapto, halo, cyano, or $NR^aR^b$;

$R_4$ is H, hydroxy, $(C_1-C_{15})$alkyl, $(C_2-C_{15})$alkenyl, $(C_2-C_{15})$alkynyl, $(C_1-C_{15})$alkoxy, $(C_1-C_{15})$alkylthio, $(C_1-C_{15})$alkanoyl, $(C_1-C_{15})$alkoxycarbonyl, $(C_2-C_{15})$alkanoyloxy, halo, cyano, trifluoromethyl, trifluoromethoxy, nitro, or $NR^cR^d$;

$R_5$ is aryl or heteroaryl, which aryl or heteroaryl is substituted with one or more groups $R^x$, and which aryl or heteroaryl is also optionally substituted with one or more halo, hydroxy, cyano, trifluoromethyl, trifluoromethoxy, $NR^eR^f$, $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, $-P(=O)(OH)_2$ or $(C_2-C_{15})$alkanoyloxy;

$R^a$ and $R^b$ are each independently H, $(C_1-C_6)$alkyl, or $(C_1-C_{15})$alkanoyl;

$R^c$ and $R^d$ are each independently H, $(C_1-C_6)$alkyl, or $(C_1-C_{15})$alkanoyl;

$R^e$ and $R^f$ are each independently H, $(C_1-C_6)$alkyl, or $(C_1-C_{15})$alkanoyl; each $R^x$ is independently $R^y$ or $-CH=CH-R^y$;

each $R^y$ is independently aryl or heteroaryl, which aryl or heteroaryl is optionally substituted with one or more groups independently selected from hydroxy, $(C_1-C_6)$alkyl, $(C_2-C_6)$alkenyl, $(C_2-C_6)$alkynyl, $(C_1-C_6)$alkoxy, $(C_1-C_6)$alkylthio, $(C_1-C_6)$alkanoyl, $(C_1-C_6)$alkoxycarbonyl, $(C_2-C_6)$alkanoyloxy, halo, cyano, trifluoromethyl, trifluoromethoxy, nitro, and $NR^vR^w$; wherein each $R^v$ and $R^w$ is independently H, $(C_1-C_6)$alkyl, or $(C_1-C_{15})$alkanoyl; and the bond represented by ----- is a single or a double bond;

wherein any $(C_1-C_{15})$alkyl, $(C_2-C_{15})$alkenyl, $(C_2-C_{15})$alkynyl, $(C_1-C_{15})$alkoxy, $(C_1-C_{15})$alkylthio, $(C_1-C_{15})$alkanoyl, $(C_1-C_{15})$alkoxycarbonyl, or $(C_2-C_{15})$alkanoyloxy, of $R_1-R_4$ is optionally substituted with one or more halo, hydroxy, cyano, or oxo (=O);

or a pharmaceutically acceptable salt thereof.

The invention also provides a pharmaceutical composition comprising a compound of formula (I), or a pharmaceutically acceptable salt thereof, in combination with a pharmaceutically acceptable diluent or carrier.

Additionally, the invention provides a therapeutic method for treating cancer comprising administering to a mammal in need of such therapy, an effective amount of a compound of formula (I), or a pharmaceutically acceptable salt thereof.

The invention also provides a compound of formula (I) for use in medical therapy (e.g. for use in treating cancer), as well as the use of a compound of formula (I) for the manufacture of a medicament useful for the treatment of cancer in a mammal, such as a human.

The invention also provides a compound of formula (I), or a pharmaceutically acceptable salt thereof for the prophylactic or therapeutic treatment of cancer.

The invention also provides a method for identifing the sub-cellular localization of the target of the schweinfurthins comprising contacting cells with a fluoresent schweinfurthin analog (e.g. a compound of formula I or II) and detecting the location of the fluorescent compound in the cells in order to identify the sub-cellular localization of the target of the schweinfurthins.

The invention also provides processes and intermediates disclosed herein that are useful for preparing compounds of formula (I) as well as other Schweinfurthin analogs.

DETAILED DESCRIPTION

The following definitions are used, unless otherwise described: alkyl, alkoxy, alkenyl, alkynyl, etc. denote both straight and branched groups; but reference to an individual radical such as propyl embraces only the straight chain radical, a branched chain isomer such as isopropyl being specifically referred to. Alkenyl denotes a hydrocarbon chain with one or more (1, 2, 3, or 4) double bonds. Likewise, alkynyl denotes a hydrocarbon chain with one or more (1, 2, 3, or 4) triple bonds. Aryl denotes a phenyl radical or an ortho-fused bicyclic carbocyclic radical having about nine to ten ring atoms in which at least one ring is aromatic; and heteroaryl encompasses a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

The term "enantiomerically enriched" as used herein refers to mixtures that have one enantiomer present to a greater extent than another. In one embodiment of the invention, the term "enantiomerically enriched" refers to a mixture having at least about 2% ee; in another embodiment of the invention, the term "enantiomerically enriched" refers to a mixture having at least about 5% ee; in another embodiment of the invention, the term "enantiomerically enriched" refers to a mixture having at least about 20% ee; in another embodiment of the invention, the term "enantiomerically enriched" refers to a mixture having at least about 50% ee; in another embodiment of the invention, the term "enantiomerically enriched" refers to a mixture having at least about 80% ee; in another embodiment of the invention, the term "enantiomerically enriched" refers to a mixture having at least about 90% ee; in another embodiment of the invention, the term "enantiomerically enriched" refers to a mixture having at least about 95% ee; in another embodiment of the invention, the term "enantiomerically enriched" refers to a mixture having at least about 98%; in another embodiment of the invention, the term "enantiomerically enriched" refers to a mixture having at least about 99% ee.

The term "enantiomerically enriched" includes enantiomerically pure mixtures which are mixtures that are substantially free of the species of the opposite optical activity or one enantiomer is present in very low quantities, for example, 0.01%, 0.001% or 0.0001%.

The term "protecting group" or "blocking group" refers to any group which, when bound to a hydroxy prevents undesired reactions from occurring at this group and which can be removed by conventional chemical or enzymatic steps to reestablish the hydroxyl group. The particular removable blocking group employed is not critical and preferred removable hydroxyl blocking groups include conventional substituents such as allyl, benzyl, acetyl, chloroacetyl, thiobenzyl, benzylidine, phenacyl, methyl methoxy, silyl ethers (e.g., t-butyl-diphenylsilyl or t-butylsilyl ("TBS")) and any other group that can be introduced chemically onto a hydroxyl functionality and later selectively removed either by chemical or enzymatic methods in mild conditions compatible with the nature of the product. Suitable hydroxyl protecting groups are known to those skilled in the art and disclosed in more detail in T. W. Greene, *Protecting Groups In Organic Synthesis*; Wiley: N.Y., 1981, and the references cited therein.

Specific values listed below for radicals, substituents, and ranges, are for illustration only; they do not exclude other defined values or other values within defined ranges for the radicals and substituents.

Specifically, $(C_1-C_{15})$alkyl can be methyl, ethyl, propyl, isopropyl, butyl, iso-butyl, sec-butyl, t-butyl, pentyl, 3-pentyl, hexyl, heptyl, octyl, nonyl, decyl, do-decyl, hexadecyl, octadecyl, icosyl; $(C_1-C_{15})$alkoxy can be methoxy, ethoxy, propoxy, isopropoxy, butoxy, iso-butoxy, sec-butoxy, pentoxy, 3-pentoxy, or hexyloxy; $(C_2-C_{15})$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_{15})$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_3-C_8)$cycloalkyl can be cyclopropyl, cyclobutyl, cyclopentyl, cyclohexyl, cycloheptyl, or cyclooctyl; $(C_1-C_{15})$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; $(C_1-C_{15})$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_{15})$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

In one specific embodiment of the invention the compound of formula (I) is not the compound,

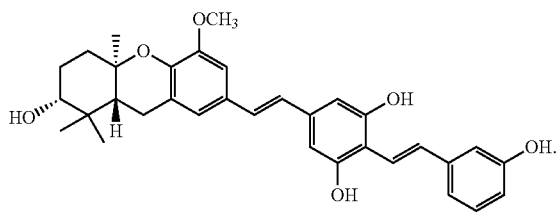 [SMILES: COc1cc(/C=C/c2cc(O)c(/C=C/c3cccc(O)c3)c(O)c2)cc2c1O[C@]1(C)CC[C@@H](O)C(C)(C)[C@H]1C2]

In one specific embodiment the invention provides a compound of formula (II):

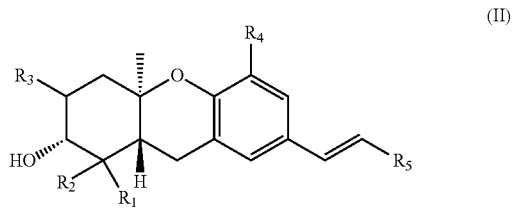

wherein:

$R_1$ and $R_2$ are each independently H, $(C_1-C_6)$alkyl, halo $(C_1-C_6)$alkyl or $(C_3-C_8)$cycloalkyl; or one of $R_1$ and $R_2$ is carboxy and the other is H, $(C_1-C_6)$alkyl, halo$(C_1-C_6)$alkyl or $(C_3-C_8)$cycloalkyl;

$R_3$ is H, $(C_1-C_{15})$alkyl, $(C_2-C_{15})$alkenyl, $(C_2-C_{15})$alkynyl, $(C_1-C_{15})$alkoxy, $(C_1-C_{15})$alkylthio, $(C_1-C_{15})$alkanoyl, $(C_1-C_{15})$alkoxycarbonyl, $(C_2-C_{15})$alkanoyloxy, hydroxy, mercapto, halo, cyano, or $NR^aR^b$;

$R_4$ is H, hydroxy, $(C_1-C_{15})$alkyl, $(C_2-C_{15})$alkenyl, $(C_2-C_{15})$alkynyl, $(C_1-C_{15})$alkoxy, $(C_1-C_{15})$alkylthio, $(C_1-C_{15})$alkanoyl, $(C_1-C_{15})$alkoxycarbonyl, $(C_2-C_{15})$alkanoyloxy, halo, cyano, trifluoromethyl, trifluoromethoxy, nitro, or $NR^cR^d$;

$R_5$ is aryl or heteroaryl, which aryl or heteroaryl is substituted with one or more groups $R^x$, and which aryl or heteroaryl is also optionally substituted with one or more halo, hydroxy, cyano, trifluoromethyl, trifluoromethoxy, $NR^eR^f$, $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, —P(=O)(OH)$_2$ or $(C_2-C_{15})$alkanoyloxy;

$R^a$ and $R^b$ are each independently H, $(C_1-C_6)$alkyl, or $(C_1-C_{15})$alkanoyl;

$R^c$ and $R^d$ are each independently H, $(C_1-C_6)$alkyl, or $(C_1-C_{15})$alkanoyl;

$R^e$ and $R^f$ are each independently H, $(C_1-C_6)$alkyl, or $(C_1-C_{15})$alkanoyl; each $R^x$ is independently $R^y$, —CH$_2$CH$_2$—$R^y$, or —CH=CH—$R^y$; and each $R^y$ is independently aryl or heteroaryl which aryl or heteroaryl is optionally substituted with one or more groups independently selected from hydroxy, $(C_1-C_6)$alkyl, $(C_2-C_6)$alkenyl, $(C_2-C_6)$alkynyl, $(C_1-C_6)$alkoxy, $(C_1-C_6)$alkylthio, $(C_1-C_6)$alkanoyl, $(C_1-C_6)$alkoxycarbonyl, $(C_2-C_6)$alkanoyloxy, halo, cyano, trifluoromethyl, trifluoromethoxy, nitro, and $NR^vR^w$; wherein each $R^v$ and $R^w$ is independently H, $(C_1-C_6)$alkyl, or $(C_1-C_{15})$alkanoyl;

wherein any $(C_1-C_{15})$alkyl, $(C_2-C_{15})$alkenyl, $(C_2-C_{15})$alkynyl, $(C_1-C_{15})$alkoxy, $(C_1-C_{15})$alkylthio, $(C_1-C_{15})$alkanoyl, $(C_1-C_{15})$alkoxycarbonyl, or $(C_2-C_{15})$alkanoyloxy, of $R_1-R_4$ is optionally substituted with one or more halo, hydroxy, cyano, or oxo (=O).

In one specific embodiment of the invention $R_1$ is H.
In one specific embodiment of the invention $R_1$ is $(C_1-C_6)$alkyl.
In one specific embodiment of the invention $R_1$ is methyl.
In one specific embodiment of the invention $R_2$ is H.
In one specific embodiment of the invention $R_2$ is $(C_1-C_6)$alkyl.
In one specific embodiment of the invention $R_2$ is methyl.
In one specific embodiment of the invention $R_3$ is H.
In one specific embodiment of the invention $R_3$ is hydroxy, amino, or mercapto.
In one specific embodiment of the invention $R_4$ is H.
In one specific embodiment of the invention $R_4$ is nitro.
In one specific embodiment of the invention $R_4$ is hydroxy.
In one specific embodiment of the invention $R_4$ is $(C_1-C_{15})$alkoxy.
In one specific embodiment of the invention $R_4$ is methoxy.
In one specific embodiment of the invention $R_5$ is aryl that is substituted with one or two groups $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.

In one specific embodiment of the invention $R_5$ is aryl that is substituted with one group $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.

In one specific embodiment of the invention $R_5$ is aryl that is substituted with one group $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.

In one specific embodiment of the invention $R_5$ is phenyl that is substituted with one or two groups $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.

In one specific embodiment of the invention $R_5$ is phenyl that is substituted with one group $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.

In one specific embodiment of the invention $R_5$ is phenyl that is substituted with one group $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.

In one specific embodiment of the invention $R_5$ is of the formula

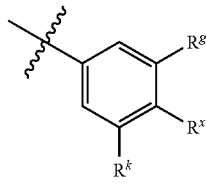

wherein:

$R^g$ and $R^k$ are each independently H, halo, hydroxy, $(C_1-C_{15})$alkyl, $(C_2-C_{15})$alkenyl, $(C_2-C_{15})$alkynyl, $(C_1-C_{15})$alkoxy, methoxymethoxy, and $(C_2-C_{15})$alkanoyloxy; wherein any $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy of $R^g$ and $R^k$ is optionally substituted with one or more halo, hydroxy, cyano, or oxo (=O).

In one specific embodiment of the invention $R_5$ is of the formula

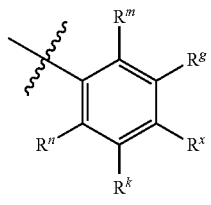

wherein:

$R^g$ and $R^k$ are each independently H, halo, hydroxy, $(C_1-C_{15})$alkyl, $(C_2-C_{15})$alkenyl, $(C_2-C_{15})$alkynyl, $(C_1-C_{15})$alkoxy, methoxymethoxy, and $(C_2-C_{15})$alkanoyloxy;

$R^m$ is H, cyano, fluoro, or —P(=O)(OH)$_2$; and
$R^n$ is H, cyano, fluoro, or —P(=O)(OH)$_2$;

wherein any $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy of $R^g$ and $R^k$ is optionally substituted with one or more halo, hydroxy, cyano, or oxo (=O).

In one specific embodiment of the invention $R^g$ and $R^k$ are each independently H, fluoro, chloro, bromo, hydroxy, or methoxy.

In one specific embodiment of the invention $R^g$ and $R^k$ are each hydroxy.

In one specific embodiment of the invention $R_5$ is heteroaryl that is substituted with one or two groups $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.

In one specific embodiment of the invention $R_5$ is heteroaryl that is substituted with one group $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.

In one specific embodiment of the invention $R_5$ is heteroaryl that is substituted with one group $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.

In one specific embodiment of the invention $R_5$ is an isoxazolyl, imadazolyl, pyridyl, indolyl, or benzo[b]furanyl ring that is substituted with one group $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.

In one specific embodiment of the invention each $R^x$ is independently $R^y$.

In one specific embodiment of the invention each $R^x$ is independently —CH═CH—$R^y$.

In one specific embodiment of the invention each $R^y$ is independently aryl, which is optionally substituted with one or more groups independently selected from hydroxy, $(C_1-C_6)$alkyl, $(C_2-C_6)$alkenyl, $(C_2-C_6)$alkynyl, $(C_1-C_6)$alkoxy, $(C_1-C_6)$alkylthio, $(C_1-C_6)$alkanoyl, $(C_1-C_6)$alkoxycarbonyl, $(C_2-C_6)$alkanoyloxy, halo, cyano, trifluoromethyl, trifluoromethoxy, nitro, and $NR'R^w$; wherein each $R^v$ and $R^w$ is independently H, $(C_1-C_6)$alkyl, or $(C_1-C_{15})$alkanoyl.

In one specific embodiment of the invention each $R^y$ is independently heteroaryl, which is optionally substituted with one or more groups independently selected from hydroxy, $(C_1-C_6)$alkyl, $(C_2-C_6)$alkenyl, $(C_2-C_6)$alkynyl, $(C_1-C_6)$alkoxy, $(C_1-C_6)$alkylthio, $(C_1-C_6)$alkanoyl, $(C_1-C_6)$alkoxycarbonyl, $(C_2-C_6)$alkanoyloxy, halo, cyano, trifluoromethyl, trifluoromethoxy, nitro, and $NR'R^w$; wherein each $R^v$ and $R^w$ is independently H, $(C_1-C_6)$alkyl, or $(C_1-C_{15})$alkanoyl.

In one specific embodiment of the invention each $R^y$ is independently phenyl, which is optionally substituted with one or more groups independently selected from hydroxy, $(C_1-C_6)$alkyl, $(C_2-C_6)$alkenyl, $(C_2-C_6)$alkynyl, $(C_1-C_6)$alkoxy, $(C_1-C_6)$alkylthio, $(C_1-C_6)$alkanoyl, $(C_1-C_6)$alkoxycarbonyl, $(C_2-C_6)$alkanoyloxy, halo, cyano, trifluoromethyl, trifluoromethoxy, nitro, and $NR'R^w$; wherein each $R^v$ and $R^w$ is independently H, $(C_1-C_6)$alkyl, or $(C_1-C_{15})$alkanoyl.

In one specific embodiment of the invention each $R^y$ is independently phenyl which is optionally substituted with one or more groups independently selected from hydroxy, $(C_1-C_6)$alkyl, $(C_2-C_6)$alkenyl, $(C_1-C_6)$alkoxy, $(C_1-C_6)$alkoxycarbonyl, $(C_2-C_6)$alkanoyloxy, halo, cyano, trifluoromethyl, trifluoromethoxy, nitro, and $NR'R^w$; wherein each $R^v$ and $R^w$ is independently H, $(C_1-C_6)$alkyl, or $(C_1-C_{15})$alkanoyl.

In one specific embodiment of the invention each $R^y$ is independently phenyl which is substituted with nitro or amino.

In one specific embodiment of the invention the compound of formula (I) is selected from:

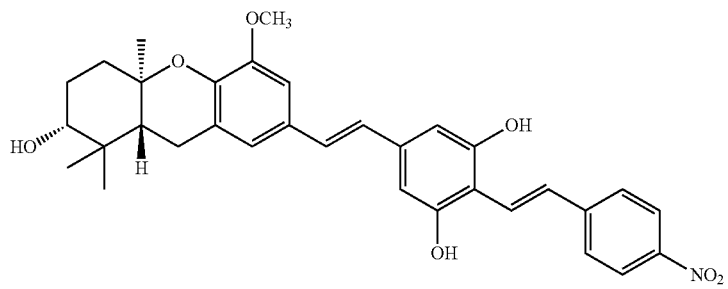

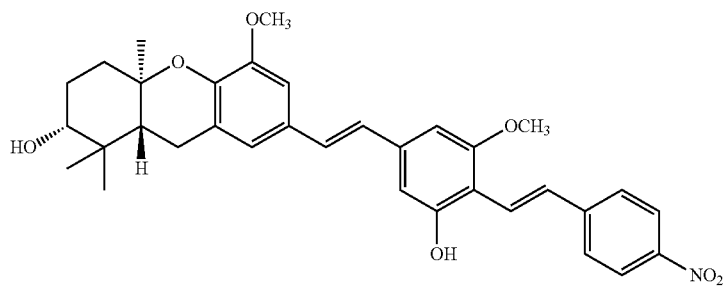

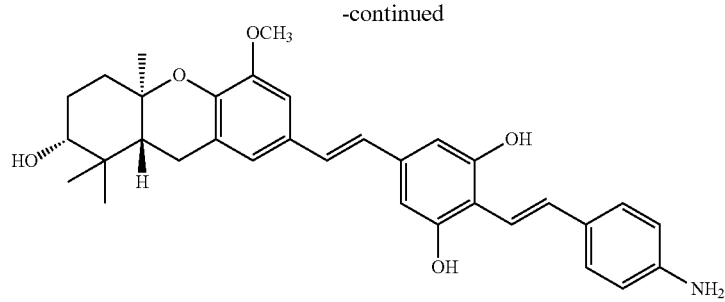
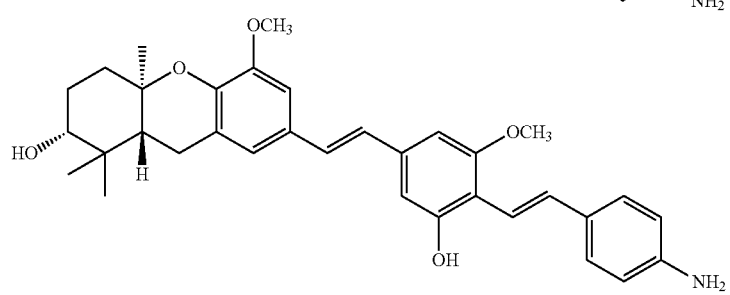
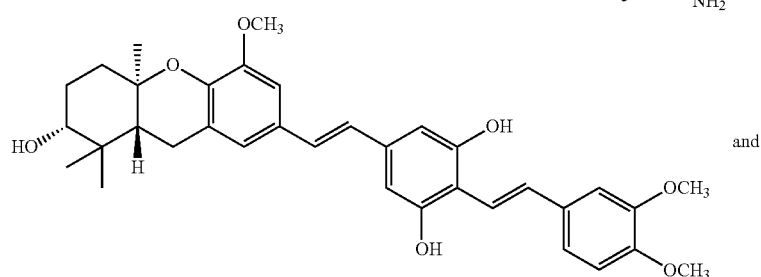 and
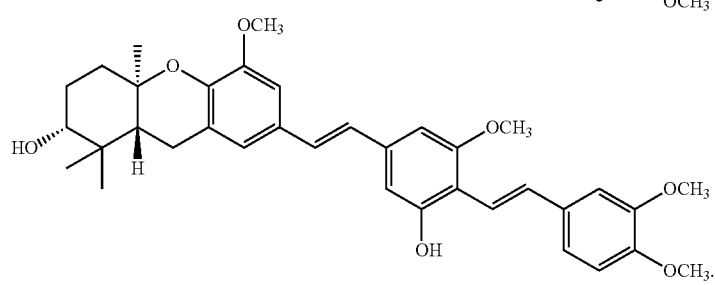
In one specific embodiment of the invention the compound of formula (I) is selected from:
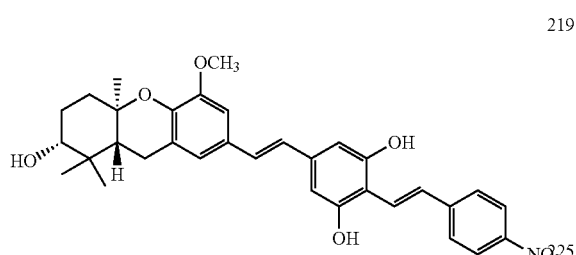
219
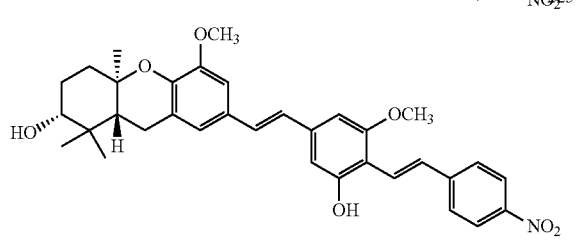
225
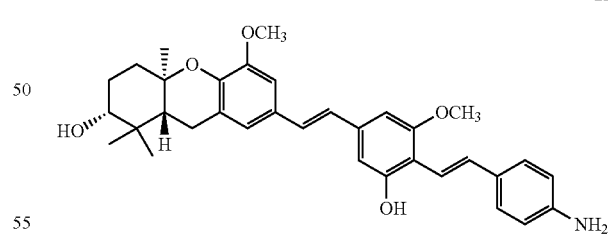
227
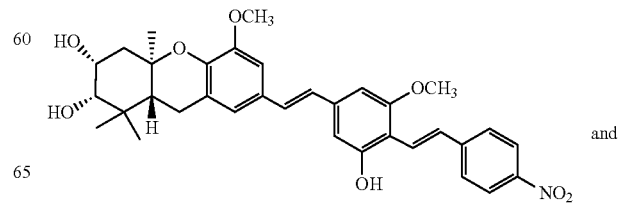 and
235

237

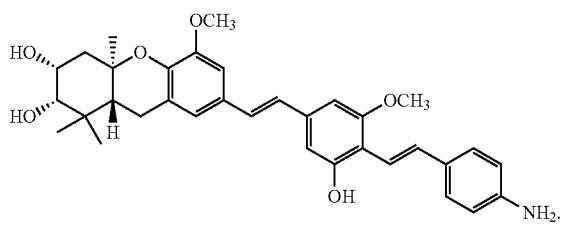

In one specific embodiment of the invention the compound of formula (I) is isolated and purified.

In one specific embodiment the invention provides a compound which is enantiomerically enriched and has an enantiomeric excess of at least about 90%.

In one specific embodiment the invention provides a compound which is enantiomerically enriched and has an enantiomeric excess of at least about 95%.

In one specific embodiment the invention provides a compound which is enantiomerically enriched and has an enantiomeric excess of at least about 98%.

In one specific embodiment the invention provides a compound which is enantiomerically enriched and has an enantiomeric excess of at least about 99%.

In one specific embodiment the invention provides a compound which is enantiomerically pure.

In one specific embodiment the invention provides a compound of formula (I) which is the 2S 4aS 9aS enantiomer.

In one specific embodiment the invention provides a compound of formula (I) which is the 2R 4aR 9aR enantiomer.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Suitable acids includes any organic acid suitable to catalyze the reaction, such as, trifluoroacetic acid (TFA). Suitable base includes any base suitable to catalyze the reaction, such as, triethyl amine (TEA).

As used herein, the terms "isolated" and "purified" refer to substances that are substantially free of other biological agents, for example, at least about 95%, about 98%, or about 99% pure.

As used herein, the terms "treat," "treatment," and "treating," extend to prophylaxis and include prevent, prevention, preventing, lowering, stopping or reversing the progression or severity of the condition or symptoms being treated. As such, the term "treatment" includes both medical, therapeutic, and/or prophylactic administration, as appropriate.

Compounds and pharmaceutical compositions suitable for use in the present invention include those wherein the active compound is administered in an effective amount to achieve its intended purpose. More specifically, a "therapeutically effective amount" means an amount effective to treat the disease, disorder, and/or condition. Determination of a therapeutically effective amount is well within the capacity of persons skilled in the art, especially in light of the detailed disclosure provided herein.

The pharmaceutically active compounds of the invention can be formulated as pharmaceutical compositions and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form for injection or infusion should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form. However, it will generally be desirable to administer them to the skin as compositions or formulations, in combination with a dermatologically acceptable carrier, which may be a solid or a liquid. Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the pharmaceutically active compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the pharmaceutically active compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compounds of the invention can also be administered in combination with other therapeutic agents that are effective to treat cancer.

The desired dose may conveniently be presented in a single dose or as divided doses administered at appropriate intervals, for example, as two, three, four or more sub-doses per day.

The sub-dose itself may be further divided, e.g., into a number of discrete loosely spaced administrations; such as multiple inhalations from an insufflator or by application of a plurality of drops into the eye.

General Synthetic Methods

Generally, a compound of formula (I) wherein the bond represented by ----- is a double bond can be prepared by coupling an aldehyde of formula 20 with a phosphonate of formula 21,

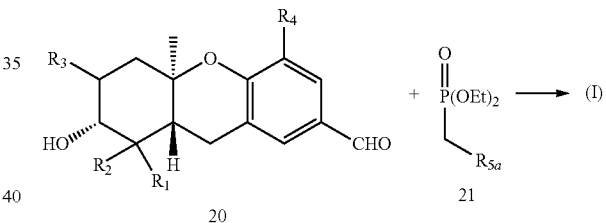

wherein $R_1$-$R_4$ have any of the values or specific values defined herein; and wherein $R_{5a}$ is a group of formula $R_5$ having any of the values or specific values defined herein or a group of formula $R_5$ that bears one or more protecting groups. When the group of formula $R_{5a}$ is a group of formula $R_5$ that bears one or more protecting groups, the compound of formula (I) can be prepared by removing the protecting groups to provide the compound of formula (I). The corresponding compounds of formula (I) wherein the bond represented by ----- is a single bond can be prepared by reduction of the olefin with magnesium in methanol. In one embodiment the invention provides a method for preparing a compound of formula I comprising reacting an aldehyde of formula 20 or a corresponding aldehyde bearing one or more protecting groups, with a phosphonate of formula 21 or a corresponding phosphonate bearing one or more protecting groups, and optionally removing any protecting groups, to provide the compound of formula I. Intermediate aldehyde 20 is particularly useful for preparing compounds of formula I, and represents one specific embodiment of the invention.

As described in the Examples herein, synthesis of the fluorescent stilbene 9 began with known aryl bromide 1 (Scheme 1).

Scheme 1. Synthesis on fluorescent schweinfurthin analog 9.

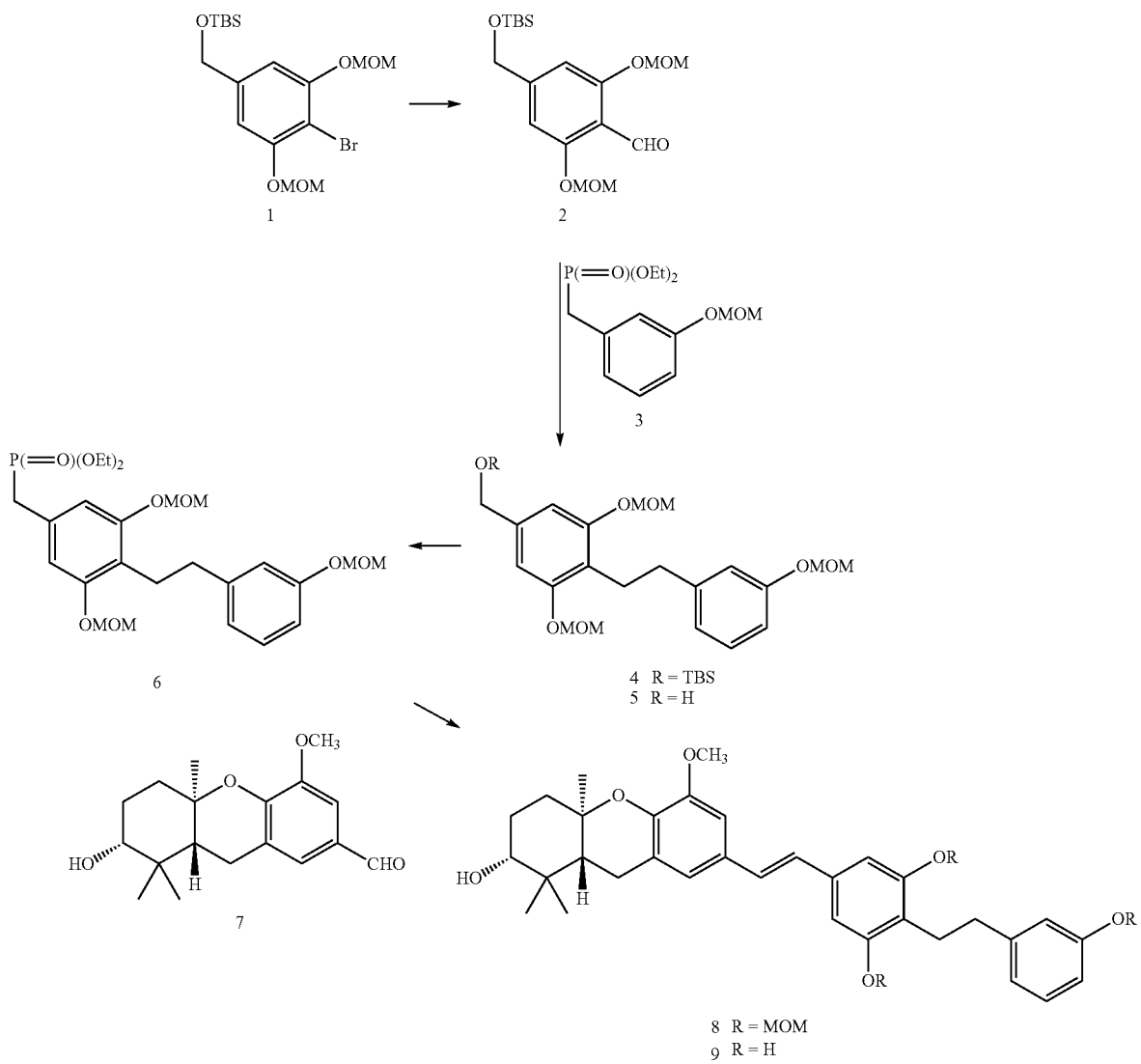

MOM = methoxymethyl

Halogen-lithium exchange of bromide 1 afforded the lithiated arene which was subsequently allowed to react with dry dimethylformamide affording the aldehyde 2 in acceptable yield. This aldehyde was treated with the known phosphonate 3 under modified Horner-Wadsworth-Emmons conditions giving the protected stilbene 4. Removal of the silyl protecting group under standard conditions gave access to the benzylic alcohol 5. A three step procedure was then used to convert the alcohol 5 into the benzylic phosphonate. Thus, treatment of the alcohol with methanesulfonyl chloride and triethyl amine affords the mesylate which can be smoothly transformed into the iodide. Displacement of the iodide by the soft nucleophile triethyl phosphite gives the desired benzylic phosphonate 6 in high yield. Another modified Horner-Wadsworth-Emmons reaction with the tricyclic aldehyde 7 gives the fully protected schweinfurthin analog 8. Removal of the MOM ether protecting groups with camphorsulfonic acid or toluenesulfonic acid gives the desired stilbene 9 in modest yields. Intermediate aldehyde 7 is particularly useful for preparing compounds of formula I, and represents one specific embodiment of the invention.

Another intermediate aldehyde that is useful for preparing compounds of formula I is a compound of formula 134:

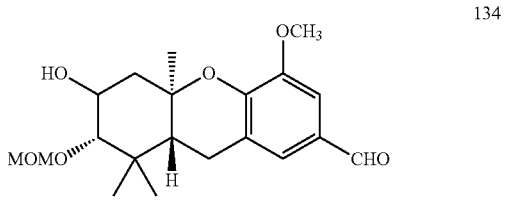

The compound of formula 134 can be prepared as illustrated below and as described in Example 2. Intermediate aldehyde 134 is particularly useful for preparing compounds of formula I, and represents one specific embodiment of the invention.

Intermediate aldehydes 134a and 134b:

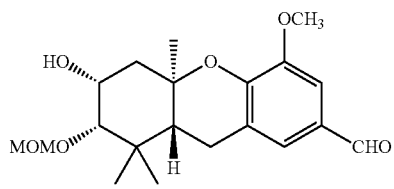

134a

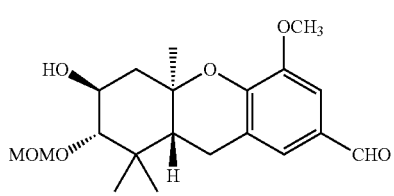

134b are also particularly useful for preparing compounds of formula I, and represents specific embodiments of the invention.

As illustrated in Schemes 2 and 3 this aldehyde can be prepared from benzyl alcohol 115, which itself was available in 3 steps and 94% overall yield from vanillin. Methylation via a Williamson ether synthesis provided compound 116, which was then exposed to n-BuLi to induce halogen metal exchange. Reaction of the resulting aryl anion with geranyl bromide (17) furnished intermediate 118 in excellent overall yield. The methyl ether 118 was easily purified by column chromatography, which allowed preparation of this intermediate on a 5- to 10-gram scale.

Scheme 2.

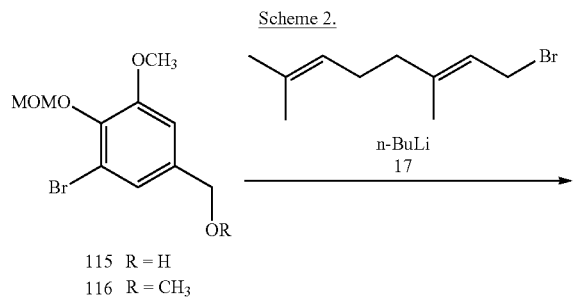

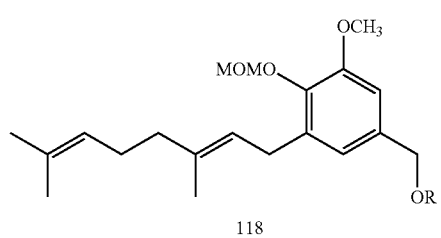

118

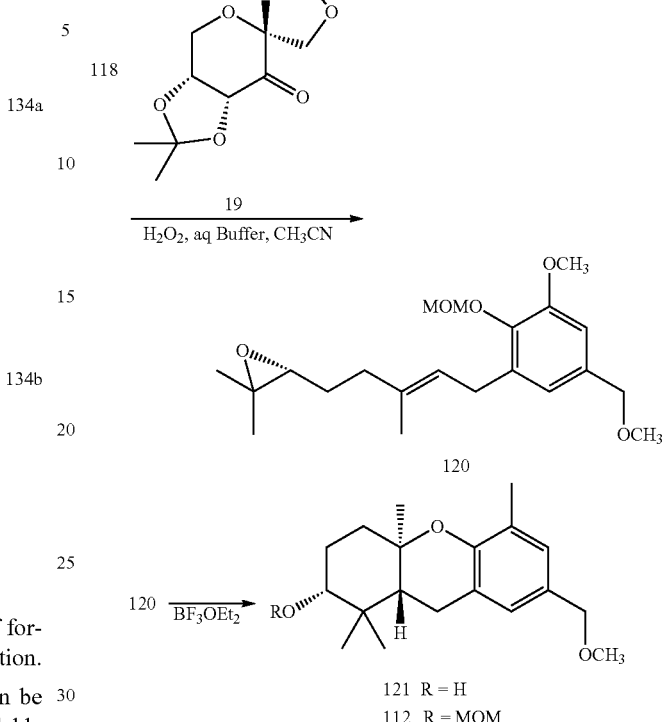

Compound 118 was epoxidized under Shi's conditions with catalyst 19. This protocol consistently produced epoxide 120 in greater than 90% ee as determined by HPLC. Although the yield for this step was modest, significant quantities of starting material were recovered and could be recycled which makes the yield based on recovered starting material more attractive (85%). Cyclization of epoxide 120 occurred upon brief exposure to $BF_3.OEt_2$ and produced a mixture of compounds 121 and 122 in excellent overall yield. The formation of this mixture was of little consequence because compounds 121 and 122 could be interconverted in excellent yield and both are useful intermediates. Hexahydroxanthene 121 was oxidized under Ley's conditions to afford ketone 124 in excellent yield (Scheme 3). Ketone 124 then served as a platform for numerous oxidations. The Rubottom approach was explored using the more reactive silyl triflates to encourage enol ether formation. Even so, conversion to the silyl enol ether was incomplete (~60%), as observed by $^1H$ NMR analysis of a reaction conducted in $CD_2Cl_2$ or by analysis of the initial product mixture. When this mixture was treated with mCPBA, the best result obtained was a 9% isolated yield of acyloin 125. Attempted MoOPH oxidation of ketone 124 afforded only recovered staring material as did the recent procedure of Tomkinson. When more forcing conditions were attempted with this oxidation, only decomposition was observed. Ketone 124 proved to be more reactive to oxidation by $O_2$ under basic conditions, but in this case the only isolated product had undergone rearrangement to an acid tentatively assigned structure 126, a product similar to one observed by Danishefsky, which may result from a Favorskii-like process.

Scheme 3.

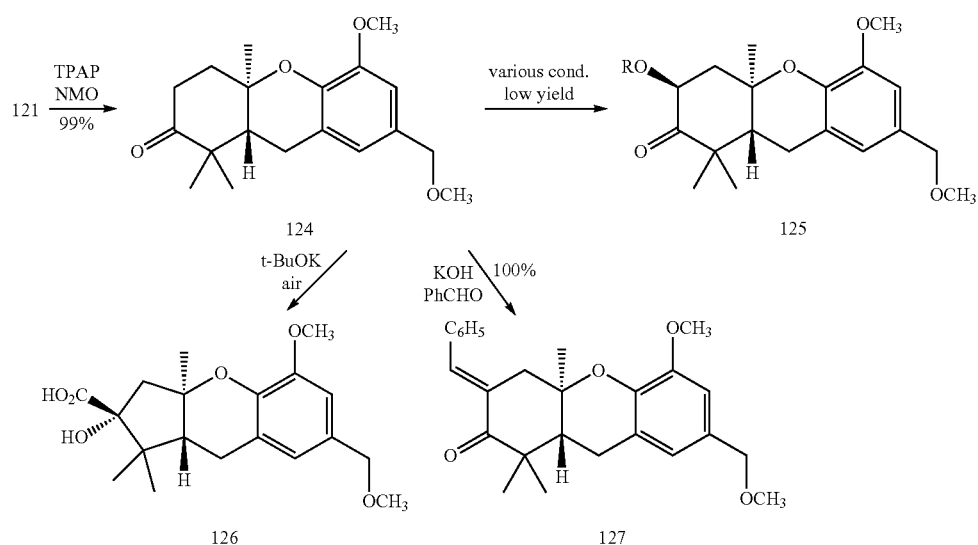

Due to the limited success of direct methods for oxidation of ketone 124 less straightforward strategies for preparation of the cis A-ring diol were considered. Furthermore, even if the yield to compound 125 could be improved, obtaining the desired diol stereoisomer from this compound might require a lengthy reaction sequence. Diffraction analysis of compound 112

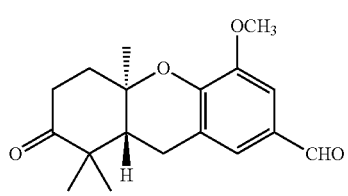

suggested that reduction would occur cleanly from the less hindered face. Therefore, a stepwise approach where reduction of a C-2 ketone was followed by reduction of a C-3 ketone to introduce that axial alcohol appeared to be promising. However, given that attempted oxidation of ketone 124 to an A-ring diketone was not straightforward, an approach based on use of an aldol condensation to generate a latent carbonyl group in the form of an olefin. After some experimentation, it was discovered that brief exposure of ketone 124 to benzaldehyde and base in ethanol produced enone 127 in quantitative yield. The availability of this enone allowed exploration of a variety of strategies for formation of a 3-keto compound.

One might reasonably assume that the limited functionality of enone 127 would enable straightforward oxidation of the exocyclic olefin (Scheme 4). However, direct treatment of compound 127 with $OsO_4/NaIO_4$ gave the complex acetal 128 as the sole product. To circumvent this problem, a more stepwise approach was pursued. Reduction of the α,β-unsaturated ketone 127 under Luche conditions afforded alcohol 129 with the desired configuration at the C-2 position as evidenced by key NOESY correlations. To stay any potential side reactions, the hindered alcohol 129 was protected as a MOM acetal under forcing conditions to afford compound 130 in moderate yield, albeit a significant amount of starting material also could be recovered. Initial attempts at oxidative cleavage of the olefin via reaction with $OsO_4/NaIO_4$ did provide a modest yield of ketone 131 (32%) along with a significant amount of diol 132. Addition of excess $NaIO_4$, use of longer reaction time, and application of a higher reaction temperature all failed to effect a complete conversion. However, the use of a more active oxidant in excess ($KMnO_4$, 10 equivalents) did provide a satisfactory yield of the ketone 131 along with significant quantities of recovered staring material even after prolonged exposure.

Scheme 4.

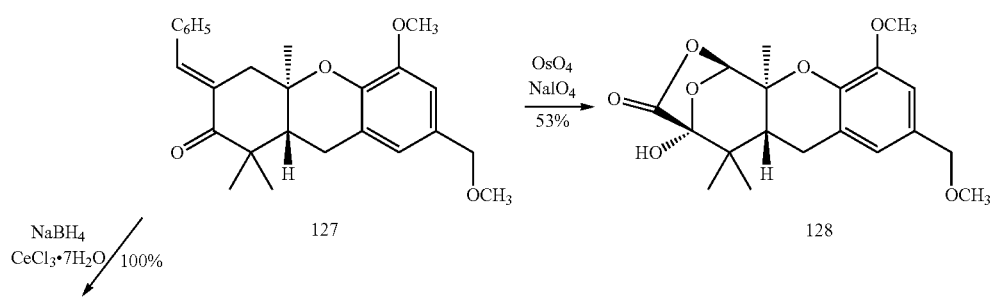

-continued

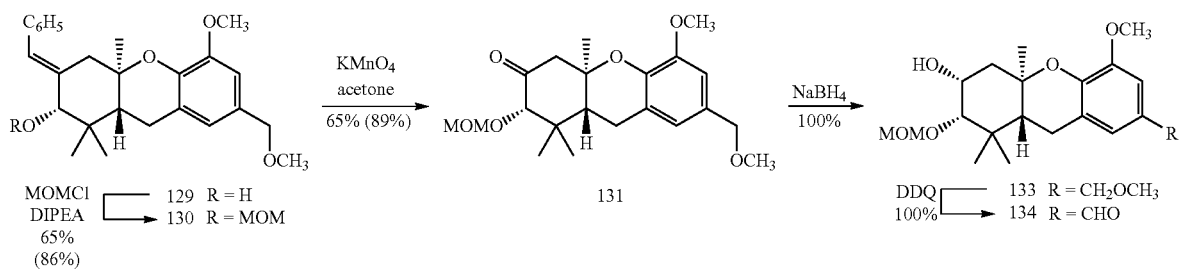

Ketone 131 was reduced upon treatment with NaBH₄ in quantitative yield to afford alcohol 133 as the only observed diastereomer. The relative stereochemistry of the C-3 center was assigned based on coupling constants: H-3 appears as a quartet with J=3.2 Hz. Exposure of compound 133 to DDQ afforded aldehyde 134 directly from the methyl ether.

Compounds of formula I (e.g. compounds 219, 225, 227, 235, and 237) can be prepared as illustrated below and as described in Examples 3-7.

As illustrated in Scheme 5 the synthesis of the p-nitro analog 219 began with the known aldehyde 212 (Neighbors, J. D., et al., 2009, *Biorganic & Medicinal Chemistry Letters*).

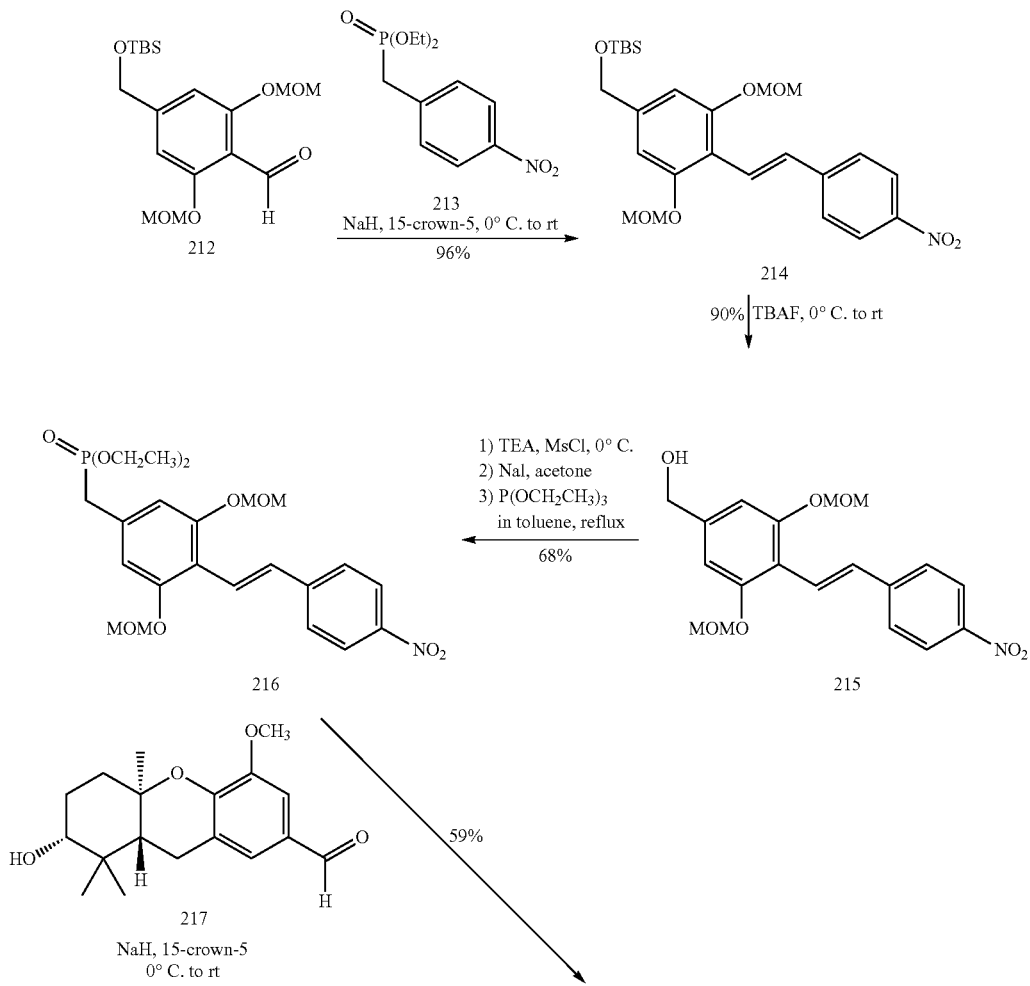

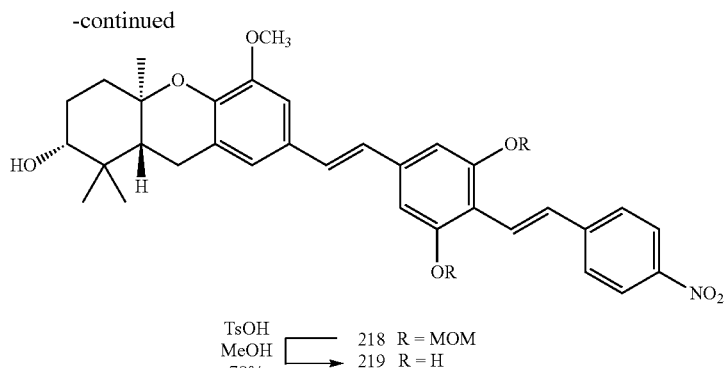

Treatment under Horner-Wadsworth-Emmons conditions with known p-nitrobenzyl phosphonate (213) afforded the protected stilbene 214. Deprotection of the silyl ether using TBAF gave free alcohol 215 in high yield. Using a three step process to convert the benzyl alcohol 215 to the phosphonate 216 through the intermediate mesylate and iodide affords desired compound in moderate yield. Coupling of this stilbene phosphonate 216 with the known aldehyde 217 (also 7) gives the bis-stilbene 218. Removal of the methoxymethyl ethers using p-toluene sulfonic acid in methanol gave the target nitro bis-stilbene 219.

The synthesis of the required methyl ether for preparing compounds of formulae 225, 227, 235, and 237 began with the known benzylic alcohol 220 (Scheme 6). Directed ortho metallation (DoM) followed by treatment of the resulting dianion with DMF afforded the desired aldehyde 221 in modest yield.

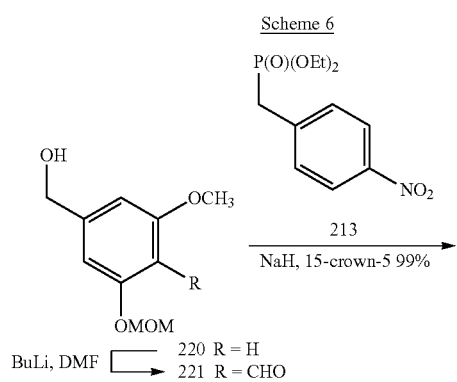

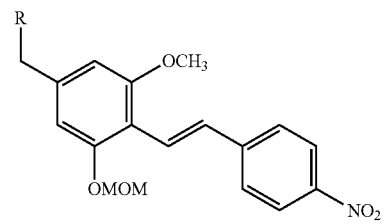

Treatment of the aldehyde 221 with phosphonate 213 gave the benzylic alcohol 222 in excellent yield. Conversion of the alcohol to the phosphonate afforded compound 223. Using DMF as the solvent for the final Arbuzov reaction of this sequence greatly improves the outcome in these sparingly soluble stilbene systems.

As illustrated in Scheme 7, condensation of the phosphonate 223 with aldehyde 217 afforded a good yield of compound 224.

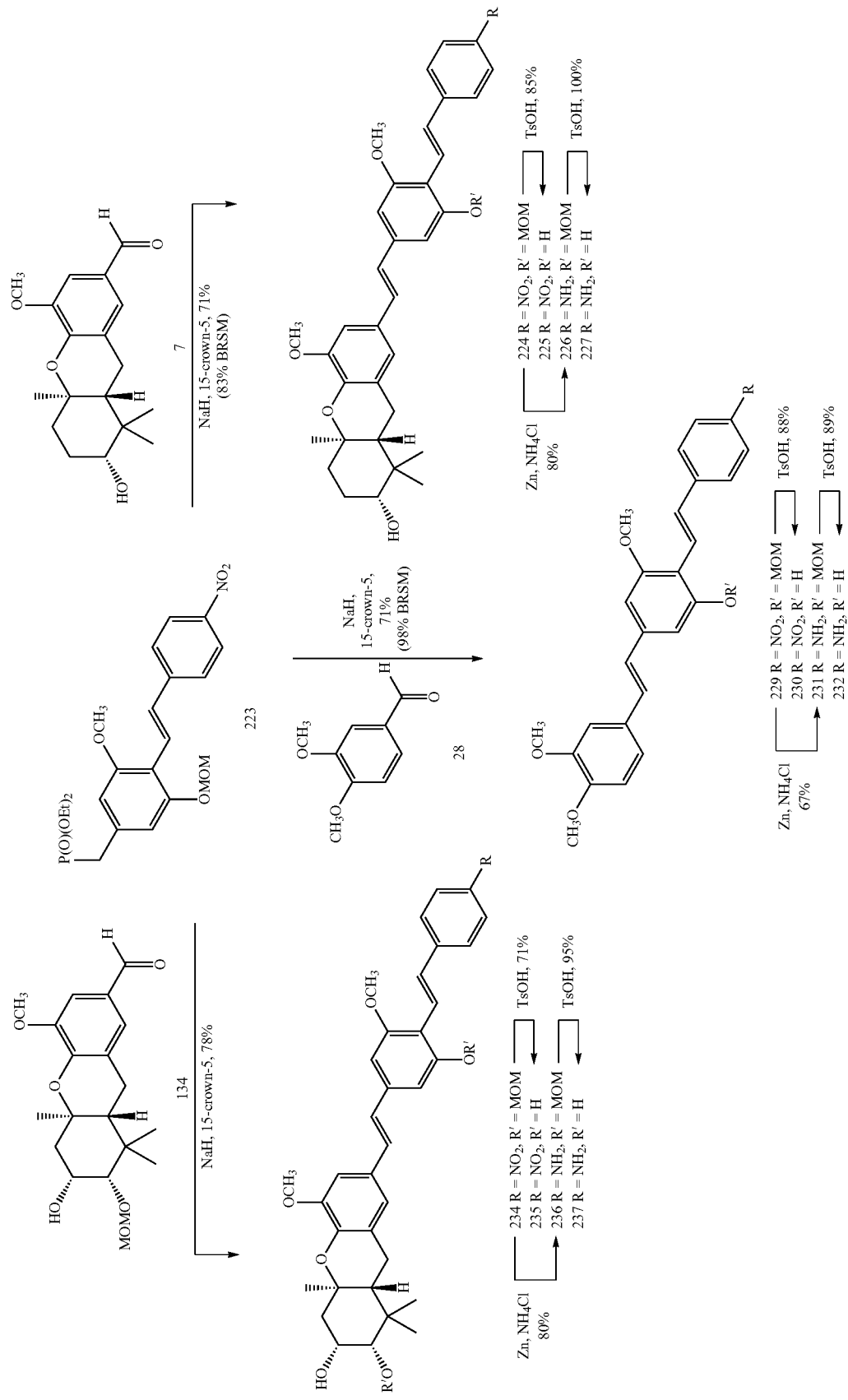

Removal of the single methoxymethyl ether protecting group afforded compound 225 in excellent yield. This compound displayed only slightly diminished activity and to the parent resorcinol and more importantly demonstrated much improved stability.

The nitro-stilbene 225 could in principle be used to identify the sub-cellular localization of the target of the schweinfurthins. In order for this to be truly informative it was determined that a fluorescent control compound lacking important pharmacophore elements would be highly useful. Reduction of the nitro group allowing entrance to amine analogues which could be used as a point of attachment to aldehyde decorated solid supports was also envisioned. These then could be used for chromatographic style isolation of interacting cellular components. Rounding out the set of desired compounds would then be the amine analogue of the control compound without the schweinfurthin warhead, and nitro and amine containing compounds based on the newly available schweinfurthin B A-ring diol system. These design priorities led to the identification of stilbenes 230, and 232 as fluorescent controls, and to stilbenes 227, and 237 as amine substituted targets.

The synthesis of these additional analogues was relatively straightforward. Condensation of the phosphonate 223 with the known aldehydes 7 and 134 gave the protected stilbenes 229 and 234. Deprotection of the methoxymethyl ethers of each of the nitro compounds 229 and 234 afforded the targets 230 and 235 in good yields. Reduction of the nitro groups of compounds 224, 229 and 234 could be carried out using sodium dithionate, however it was subsequently found that Zn in ammonium chloride could also be used for this transformation affording the desired amines 226, 231, and 236. Again deprotection of these compounds was uneventful affording compounds 227, 232, and 237.

The target compounds all exhibited fluorescence (Table 1). The nitro-compounds 219, 225, 230, and 235 all displayed larger stokes shifts than the amine compounds 227, 232 and 237. The nitro substituted compounds also demonstrate significantly red-shifted absorbtion and emission maxima compared to the previously synthesized meta-phenol bis-stilbene 210. This shift to the green region for the fluorescence emission allows cellular studies on these compounds without any interference from autofluoescence.

TABLE 1

| Compound | Absorbtion Maximum | Emission Maximum | Extinction Coefficient | Concentartion uM |
| --- | --- | --- | --- | --- |
| 219 | 426 | 593 | 26500 | 50 uM |
| 225 | 429 | 557 | 17902 | 50 uM |
| 230 | 431 | 579 | 24400 | 50 uM |
| 227 | 377 | 493 | 33600 | 50 uM |

The anti-cancer activity of a compound of the invention may be determined using pharmacological models which are well known to the art, for example, NCI 60-cell line anticancer assay. Representative compounds of formula (I) were tested and were found to have anti-cancer activity in this assay.

The effect of a compound of the invention on cancer cell morphology may be determined using pharmacological models which are well known to the art, or it may be determined using Test A below.

Test A

Cell Culture—SF-295 cells were maintained in RPMI 1640 supplemented with 10% fetal calf serum, and penstreptamycin. A-549 cells were maintained in F-12 media with 10% fetal calf serum and penstreptamycin. Both cell lines were incubated at 37° C. and 5% $CO_2$.

Cellular Morphology—Cells were plated on sterilized coverslips in 6-well plates and allowed to reach 65% confluency before treatment with indicated compounds. At the conclusion of the treatment interval, cells were rinsed and fixed with 3.7% formaldehyde for 15 minutes. After subsequent rinses in PBS, cells were permeabilized with 0.2% triton X-100 for 4 minutes and rinsed in PBS. Cells were then incubated with 1% BSA for 30 minutes before incubation with phalloidin stain (Molecular Probes, Eugene, Oreg.) for 20 minutes. At the completion of staining interval, cells were rinsed and mounted using Vectashield mounting media containing DAPI (Vector laboratories, Inc., Burlingame, Calif.). Slides were imaged using a Bio-Rad Multi-photon microscope and processed using Image-J software.

In the NCI's 60 cancer cell screen, SF-295 cells are amongst the most sensitive cell lines to schweinfurthin induced growth inhibition. In addition to their effects on cellular growth, schweinfurthins induce drastic changes in cell morphology at time points beyond 24 hours. In culture, SF-295 cells are large polygonal shaped cells with multiple outstretched focal adhesions. Treatment of SF-295 cells with schweinfurthins such as 3-dSB, induces changes hallmarked by a decrease in cell area and a reduction in F-actin, which results in spindle-shaped cells with F-actin staining only at the periphery of these cells.

The treatment of SF-295 cells for 24 hours with compound 9 (500 nM) or 3-dSB (500 nM) displayed morphologic characteristics similar to control cells. However at 48 hours cells treated with 3-dSB (500 nM) or compound 9 (500 nM) display characteristic changes in cell morphology. These changes appear to differ from those induced by the ROCK inhibitor Y-27632 (10 μM), which caused jagged F-actin at the periphery and long slender projections to form. In addition ROCK inhibition induces changes at 24 hours. At equivalent concentrations compound 9 displays similar activity as 3-dSB in SF-295 cells, yet both compound 9 and 3-dSB differ from the activity of Y-27632.

The schweinfurthins display large differential, which means that some cell lines are less sensitive to schweinfurthins. One of these cell lines is the A-549 (human lung carcinoma) cell line. A-549 cells are rectangular and cover less surface area in comparison to SF-295 cells. Treatment with 3-dSB (500 nM) or compound 9 (500 nM) does not induce a morphologic change at 24 hours or 48 hours. The absence of change is consistent with previous studies which indicate that A549 cells are less sensitive to schweinfurthin treatment. Similar to the effects in SF-295 cells, Y-27632 (10 μM) induces ruffled F-actin at the edges of the A-549 cells. These findings further suggest that the synthetic manipulations present in compound 9 do not alter the differential activity of the schweinfurthin compounds.

Selective toxicity is a distinguishing characteristic of the schweinfurthin compounds. Preserving the toxicity of the natural schweinfurthins is useful in the utilization of schweinfurthin analogues of formula I. Compound 9 maintains the activity of schweinfurthins in SF-295 cells and displays characteristic changes in cell morphology. These findings provide further understanding of the structure function of schweinfurthins.

The in vivo fluorescent properties of a compound of the invention may be determined using models which are well known to the art, or they may be determined using Test B below.

Test B

Fluorescence Microscopy—SF-295 cells were plated on sterilized coverslips in 6-well plates and allowed to reach 65% confluency and then treated for indicated intervals. At the conclusion of the treatment interval cells were washed three times in complete media to remove residual compound. Immediately following rinsing cells were mounted onto microscope slides and imaged using a Bio-Rad Multi-photon microscope at the University of Iowa Central Microscopy facility. Images were further processed using Image-J software.

Compounds of the invention can be used to elucidate the mechanism or schweinfurthin activity via compound localization. Indeed, SF-295 cells treated with concentrations of compound 9 as low as 100 nM could be visualized at all time points tested. Unlike previous attempts with other schweinfurthins, the fluorescence in treated cells was significantly greater than control cell fluorescence. As expected treatment of SF-295 cells with increasing concentrations of compound 9 increased fluorescence intensity at all time points tested. The localization of compound 9 within cells appears largely cytosolic with intense fluorescence in the peri-nuclear region. The fluorescent properties of compound 9 allow for its visualization which may allow for the determination of its site of action.

The anti-cancer effect of a compound of the invention can also be determined using the assay scheme discussed in Test C below.

Test C

The National Cancer Institute 60 human tumor cell line anti-cancer assay has been used for indicating the schweinfurthin-like activity of various analogues. Additionally, a three pronged approach that allows a more rapid turn around can be used. This three pronged testing scheme involves 1) MTT assay in schweinfurthin sensitive human glioma derived SF-295 cell line; 2) MTT assay in the schweinfurthin resistant human non-small cell lung cancer derived cell line A549; and 3) microscopic observation of cell morphology changes at 24 and 48 hours. Compounds displaying schweinfurthin-like activity show a dramatic change in cell morphology at concentrations consistent with anti-cancer activity. This three pronged testing scheme is a very simple method that has successfully identified compounds with and without schweinfurthin-like activity. Accordingly, in one embodiment the invention provides a method for identifying a compound with schweinfurthin-like activity comprising, subjecting the compound to 1) an MTT assay in a schweinfurthin sensitive human glioma derived SF-295 cell line; 2) an MTT assay in the schweinfurthin resistant human non-small cell lung cancer derived cell line A549; and 3) a microscopic observation of cell morphology changes at one or more preselected time points (e.g. at about 24 or 48 hours).

The nitro-substituted compound 225 and the control compound lacking the schweinfurthin left-half warhead 230 displayed activity as expected in this regard. The additional analogues synthesized here were also tested in this scheme. The free resorcinol 219 was the most potent of these compounds with almost identical activity to the standard 3-deoxyschweinfurthin B in the SF-295 cell line. Interestingly 219 is almost an order of magnitude more potent than 3-deoxyschweinfurthin B in the A549 lung cancer line. This compound still shows the significant drop in activity in the A549 line vs. the SF-295 line that is indicative of the schweinfurthin like activity. All of the compounds showed an approximately 10 fold decrease in activity in the lung cancer vs. the glioma cell line. Another indication of preservation of the novel schweinfurthin mechanism of action is found in the observation of these two cell lines as they grow with drug treatment. All of the compounds tested caused SF-295 cells to adopt a spindle shape with fewer projections than the control cells at doses one to two orders of magnitude lower than that required to cause this effect in the A549 cell line. While neither of the amine substituted analogues (227 and 237) were more potent than 3-deoxyschweinfurthin B they did show all of the hall marks of schweinfurthin like activity. Compound 237 bearing the dihydroxylated A-ring such as found in schweinfurthin A(1) and B(2) is not significantly more active than the 3-deoxy compound 227.

The invention will now be illustrated by the following non-limiting Examples.

EXAMPLES

Example 1

Synthesis of Compound 9

To a solution of stilbene 8 (16 mg, 0.024 mmol) in MeOH (5 mL) was added p-toluenesulfonic acid (3 mg, 0.014 mmol). The resulting solution was heated to 60° C. for 5 hours. The reaction was quenched by addition of saturated NaHCO$_3$, extracted with ethyl acetate, and the organic phase was washed with brine and dried over MgSO$_4$. Concentration in vacuo, followed by final purification by column chromatography (2:1 to 1:1 hexanes:ethyl acetate) afforded the bis-stilbene 9 (10 mg, 79%) as a slightly yellow oil: $^1$H NMR (CDCl$_3$) δ 7.19 (d, J=17 Hz, 1H), 7.55 (d, J=17 Hz, 1H), 7.18 (t, J=7.9 Hz, 1H), 7.04-6.98 (m, 4H), 6.95 (d, J=6.9 Hz, 2H), 6.90-6.88 (m, 1H), 6.73-6.70 (m, 2H), 3.82 (s, 3H), 3.43-3.38 (m, 1H), 2.76-2.73 (m, 2H), 1.85-1.63 (m, 6H), 1.23 (s, 3H), 1.13 (s, 3H), 0.90 (s, 3H); $^{13}$C NMR (CDCl$_3$) δ 158.5, 157.6, 150.2, 144.1, 142.1, 138.6, 131.5, 130.4, 129.7, 129.6, 126.5, 123.7, 121.8, 121.5, 118.7, 114.7, 113.0, 112.3, 108.3, 77.7, 77.6, 56.1, 47.2, 39.2, 38.7, 29.2, 27.9, 23.8, 20.4, 14.9; HRMS (EI) calcd for $C_{33}H_{36}O_6$ (M$^+$) 528.2512, found 528.2523.

The intermediate stilbene 8 was prepared as follows.

a. To a solution of the known bromide 1 (476 mg, 1.1 mmol) in THF (15 mL) at −78° C. was added n-BuLi (0.6 mL, 2.3 M in hexanes) dropwise over 2 min. After 20 mins, DMF was added (0.2 mL, 1.4 mmol, containing some CaH$_2$ as a drying agent). The reaction was allowed to progress for an additional 1 hour, and quenched by addition of saturated aq. NH$_4$Cl. The aqueous phase was extracted with EtOAc, and the combined organic phases were washed with brine, dried with MgSO$_4$, and concentrated in vacuo to afford a yellow oil. Final purification by column chromatography afforded aldehyde 2 (234 mg, 56%) as a clear oil. $^1$H NMR (CDCl$_3$) δ 10.5 (s, 1H), 6.84 (s, 2H), 5.26 (s, 4H), 4.73 (s, 2H), 3.50 (s, 6H), 0.95 (s, 9H), 0.12 (s, 6H); $^{13}$C NMR (CDCl$_3$) δ 188.9, 159.6 (2C), 151.0, 114.7, 105.6 (2C), 94.8 (2C), 64.5, 56.4 (2C), 25.8 (3C), 18.3, −5.4 (2C).

b. A suspension of NaH (290 mg, 7.8 mmol, 60% in oil), and 15-crown-5 (1 drop, cat.) in THF (10 mL) was cooled to 0° C. To this was added aldehyde 2 (168 mg, 0.45 mmol) and phosphonate 3 (185 mg, 0.64 mmol) in THF (10 mL). The mixture was allowed to warm to room temperature and stirred a total of 10 hours. Water was added dropwise, and the solution was extracted with EtOAc. The resulting organic phase was washed with brine, dried over MgSO$_4$, and concentrated in vacuo. Final purification by column chromatography (6:1 to 2:1 hexanes:ethyl acetate) gave the stilbene 4 (228 mg, 100%) as a clear oil: $^1$H NMR (CDCl$_3$) δ 7.61 (d, J=17 Hz, 1H), 7.50 (d, J=17 Hz, 1H), 7.38-7.29

(m, 3H), 7.03-7.00 (m, 1H), 6.93 (s, 2H), 5.34 (s, 4H), 5.30 (s, 2H), 4.80 (s, 2H), 3.60 (s, 6H), 3.59 (s, 3H), 1.05 (s, 9H), 0.02 (s, 6H), $^{13}$C NMR (CDCl$_3$) δ 157.4, 156.1 (2C), 142.3, 140.7, 132.0, 129.4, 120.4, 120.1, 115.1, 114.6, 114.1, 106.0 (2C), 94.8 (2C), 94.3, 64.7, 56.1 (2C), 55.9, 25.8 (3C), 18.3, −5.3 (2C). Anal. Calcd for C$_{27}$H$_{40}$O$_7$Si:C, 64.30; H, 7.99. Found: C, 64.09; H, 8.02.

c. Silyl ether 4 (227 mg, 0.45 mmol) was dissolved in THF (10 mL) and the solution was cooled to 0° C. To this solution was added TBAF (0.6 mL, 1.00 M in THF), after 5 minutes the ice bath was removed and after 4 hours the reaction was quenched with sat. NH$_4$Cl. After extraction with ethyl acetate, the combined organic extracts were washed with water and brine, dried over MgSO$_4$, and concentrated in vacuo to give the desired benzylic alcohol 5 (176 mg, 100%) as a clear oil. $^1$H NMR (CDCl$_3$) δ 7.52 (d, J=17 Hz, 1H), 7.40 (d, J=17 Hz, 1H), 7.29-7.19 (m, 3H), 6.94-6.91 (m, 1H), 6.82 (s, 2H, 5.24 (s, 4H), 5.21 (s, 2H), 4.62 (s, 2H), 3.49 (s, 9H), 2.51 (br. S 1H), $^{13}$C NMR (CDCl$_3$) δ 157.4, 156.1 (2C), 141.9, 140.5, 132.3, 129.4, 120.1, 120.1, 115.7, 114.7, 114.1, 106.7 (2C), 94.6 (2C), 94.3, 64.9, 56.2 (2C), 55.9 d. Methanesulfonyl chloride (0.15 mL, 1.9 mmol) was added to a solution of benzylic alcohol 5 (176 mg, 0.45 mmol) and Et$_3$N (0.2 mL 1.4 mmol) in CH$_2$Cl$_2$ (10 mL) and, the reaction mixture was allowed to warm to room temperature over 1 h, quenched by addition of H$_2$O, and extracted with CH$_2$Cl$_2$. The combined organic layers were washed with NH$_4$Cl (sat), brine, dried (MgSO$_4$), and concentrated in vacuo. The resulting residue and NaI (150 mg, 1.0 mmol) were stirred in acetone (10 mL) for 8 h. The reaction mixture was concentrated in vacuo to afford a red solid, which was dissolved in EtOAc. After the resulting yellow solution was washed with Na$_2$S$_2$O$_3$ until the color faded, it was washed with brine, dried (MgSO$_4$) and concentrated in vacuo. The resulting yellow oil was added to triethyl phosphite (2 mL) and the mixture was heated at 80° C. for 24 h. After the solution was allowed to cool to rt, the excess phosphite was removed at high vacuum. The initial yellow oil was purified by flash chromatography (1:2 hexanes: EtOAc to 100% EtOAc) to afford phosphonate 6 (201 mg, 88%) as a clear oil: $^1$H NMR (CDCl$_3$) δ 7.53 (d, J=16.7 Hz 1H), 7.40 (d, J=16.7 Hz, 1H), 7.28-7.21 (m, 3H), 6.97-6.94 (m, 1H), 6.80-6.79 (m, 2H), 5.26 (s, 4H), 5.23 (s, 2H), 4.12-4.02 (m, 4H), 3.52 (s, 9H), 3.13 (d, J$_{HP}$=21.8 Hz, 2H), 1.30 (t, J=7.0 Hz, 6H), $^{13}$C NMR (CDCl$_3$) δ 157.4, 155.9 (d, J$_{CP}$=3.7 Hz), 140.6, 132.3 (d, J$_{CP}$=1.6 Hz), 132.0 (d, J$_{CP}$=8.0 Hz), 129.4, 120.1, 120.1, 115.3 (d, J$_{CP}$=4.1 Hz), 114.7, 114.1, 110.2 (d, J$_{CP}$=6.7 Hz), 94.8, 94.4, 62.1 5(d, J$_{CP}$=6.8 Hz), 56.2, 55.9, 33.5 (d, J$_{CP}$=138 Hz), 16.3 (d, J$_{CP}$=6.0 Hz), HRMS (EI) clacd for C$_{25}$H$_{35}$O$_9$P (M$^+$) 510.2019 found 510.2018.

e. A suspension of NaH (98 mg, 25 mmol, 60% in oil), and 15-crown-5 (1 drop, cat.) in THF (7 mL) was cooled to 0° C. To this was added aldehyde 7 (50 mg, 0.16 mmol) and phosphonate 6 (106 mg, 0.21 mmol) in THF (8 mL). The mixture was allowed to warm to room temperature and stirred a total of 30 hours. Water was added dropwise, and the solution was extracted with EtOAc. The resulting organic phase was washed with brine, dried over MgSO$_4$, and concentrated in vacuo. Final purification by column chromatography (3:1 to 1:1 hexanes:ethyl acetate) gave the stilbene 8 (26.6 mg, 26%) as a green waxy solid oil: $^1$H NMR (CDCl$_3$) δ 7.55 (d, J=16.6 Hz, 1H), 7.43 (d, J=16.6 Hz, 1H), 7.32-7.20 (m, 4H), 7.04-6.87 (m, 6H), 5.32 (s, 4H), 5.23 (s, 2H), 3.91 (s, 3H), 3.55 (s, 6H), 3.52 (s, 3H0, 3.47-3.42 (m, 1H), 2.74-2.71 (m, 2H), 2.20-2.12 (m, 1H), 1.90-1.47 (m, 5H), 1.27 (s, 3H), 1.14 (s, 3H), 0.90 (s, 3H), $^{13}$C NMR (CDCl$_3$) δ 157.4, 156.3, 148.9, 142.7, 140.7, 137.8, 132.1, 129.5, 129.1, 128.6, 125.9, 122.6, 120.7, 120.3, 120.1, 125.7, 114.7, 114.2, 106.7, 106.4, 94.8, 94.4, 77.9, 77.1, 60.3, 56.3, 56.0, 46.7, 38.3, 37.6, 28.2, 27.3, 23.1, 19.8, 14.1; HRMS (EI) calcd for C$_{39}$H$_{48}$O$_9$ (M$^+$) 660.3298, found 660.3301.

Example 2

Synthesis of Intermediate Aldehyde 134

To a solution of methyl ether 133 (50 mg, 0.13 mmol), in CH$_2$Cl$_2$/water (4:1) at room temperature was added DDQ (34 mg, 0.15 mmol). After 80 min the reaction was quenched by addition of brine and NaHCO$_3$. The resulting solution was extracted with CH$_2$Cl$_2$, and the combined organic phases were washed with a small amount of water followed by brine. The organic phase was dried (MgSO$_4$) and concentrated in vacuo. Aldehyde 134 (48 mg, 100%) was obtained as a faintly yellow wax that was used without further purification: [α]$^{26.4}_D$=41.6° (c 1.0, CH$_3$OH, 92% ee by HPLC); $^1$H NMR (CDCl$_3$) δ 9.80 (s, 1H), 7.25 (s, 1H), 7.24 (s, 1H), 4.83 (d, J=6.6 Hz, 1H), 4.73 (d, J=6.6 Hz, 1H), 4.32 (ddd, J=3.6, 3.6, 3.6 Hz, 1H), 3.90 (s, 3H), 3.47 (s, 3H), 3.27 (d, J=3.6 Hz, 1H), 2.86-2.79 (m, 2H), 2.59 (dd, J=14.4, 3.6 Hz, 1H), 2.39 (bd, 1H), 1.98 (dd, J=14.4, 3.6 Hz, 1H), 1.79 (dd, J=13.2, 5.4 Hz, 1H), 1.49 (s, 3H), 1.13 (s, 3H), 1.11 (s, 3H); $^{13}$C NMR (CDCl$_3$) δ 191.0, 149.7, 148.5, 128.8, 127.2, 122.7, 107.5, 97.0, 84.7, 78.0, 68.6, 56.2, 56.1, 46.9, 42.1, 38.0, 28.8, 22.9, 21.8, 16.7; HRMS (ESI) m/z calcd for C$_{20}$H$_{28}$O$_6$ (M$^+$) 364.1886, found 364.1896.

The intermediate methyl ether 133 was prepared from the benzyl alcohol 115 as described below.

a. Methyl Ether 116. To a solution of the known benzyl alcohol 115 (4.42 g, 15.9 mmol, Neighbors, et al., *Tetrahedron Lett.* 2008, 49, 516-519) in THF at 0° C. was added NaH (1.2 g, 60% in oil, 30 mmol) followed by CH$_3$I (1.5 mL, 24 mmol). After 3 hours the reaction was quenched by addition of water. The resulting solution was extracted with ethyl acetate, and the organic extract was washed with brine. After the organic phase was dried (MgSO$_4$) and concentrated in vacuo, final purification by column chromatography (3:1 hexanes/ethyl acetate) afforded methyl ether 116 (4.84 g, 96%) as a yellow oil: $^1$H NMR (CDCl$_3$) δ 7.06 (s, 1H), 6.82 (s, 1H), 5.12 (s, 2H), 4.31 (s, 2H), 3.80 (s, 3H), 3.60 (s, 3H), 3.33 (s, 3H); $^{13}$C NMR (CDCl$_3$) δ 153.6, 142.8, 135.8, 124.1, 117.7, 111.0, 98.8, 73.9, 58.4, 58.1, 56.2; HRMS (ESI) m/z calcd for C$_{11}$H$_{15}$O$_4$Br (M$^+$) 290.0154, found 290.0157.

b. Genanyl Arene 118. To a solution of methyl ether 116 (2.0 g, 6.9 mmol) in THF at −78° C. was added n-BuLi (3.0 mL, 2.5 M in hexanes) over 5 min. After ~30 min geranyl bromide (17, 1.5 mL, 7.9 mmol) was added dropwise. The solution was kept cold for 50 min and quenched by addition of water. The resulting solution was extracted with ethyl acetate, and the combined organic phases were washed with brine. The organic phase was dried (MgSO$_4$) and concentrated in vacuo. Final purification by column chromatography (9:1 hexanes/ethyl acetate) afforded arene 118 (2.2 g, 91%) as a yellow oil: $^1$H NMR (CDCl$_3$) δ 6.78 (s, 1H), 6.73 (s, 1H), 5.32 (t, J=7.2 Hz, 1H), 5.13-5.10 (m, 1H), 5.07 (s, 2H), 4.37 (s, 2H), 3.84 (s, 3H), 3.59 (s, 3H), 3.43 (d, J=7.2 Hz, 2H), 3.38 (s, 3H), 2.12-2.02 (m, 4H), 1.71 (s, 3H), 1.69 (s, 3H), 1.60 (s, 3H); $^{13}$C NMR (CDCl$_3$) δ 152.1, 143.3, 136.0, 135.5, 134.0, 131.2, 124.2, 122.6, 121.0, 109.3, 98.8, 74.6, 58.0, 57.3, 55.6, 39.6, 28.2, 26.5, 25.6, 17.6, 16.0; HRMS (ESI) m/z calcd for $C_{21}H_{32}O_4$ ($M^+$) 348.2301, found 348.2309.

c. Epoxide 120. To a solution of arene 118 (2.8 g, 8.0 mmol) and Shi's catalyst (19, 590 mg, 2.1 mmol) in aq buffer (30 mL, 2 M $K_2CO_3$ and 4 mM EDTA) and organic phase (50 mL, 1:1:1 $CH_2Cl_2$/MeCN/EtOH) at 0° C. was added hydrogen peroxide (7 mL, 30%) over 7 hours. After an additional 2 hours the reaction was quenched by addition of aq $Na_2SO_3$. The resulting solution was extracted with ethyl acetate, and the combined organic phases were washed with brine. The organic phase was dried ($MgSO_4$) and concentrated in vacuo. Final purification by column chromatography (4:1 hexanes/ethyl acetate) afforded recovered starting material (0.62 g, 22%) and epoxide 120 (1.84 g, 63%) as a colorless oil: $^1$H NMR (CDCl$_3$) δ 6.75 (s, 1H), 6.69 (s, 1H), 5.34 (t, J=7.1 Hz, 1H), 5.04 (s, 2H), 4.34 (s, 2H), 3.81 (s, 3H), 3.55 (s, 3H), 3.40 (d, J=7.1 Hz, 2H), 3.35 (s, 3H), 2.68 (t, J=6.3 Hz, 1H), 2.31-2.08 (m, 2H), 1.71 (s, 3H), 1.68-1.63 (m, 2H), 1.24 (s, 3H), 1.22 (s, 3H); $^{13}$C NMR (CDCl$_3$) δ 152.0, 143.2, 135.2, 135.0, 134.0, 123.1, 120.8, 109.3, 98.7, 74.5, 64.0, 58.2, 58.0, 57.3, 55.5, 36.2, 28.2, 27.2, 24.7, 18.6, 16.0; HRMS (ESI) m/z calcd for $C_{21}H_{32}O_5$ ($M^+$) 364.2250, found 364.2262.

d. Tricyclic Ether 121. To a solution of epoxide 120 (958 mg, 2.6 mmol) in $CH_2Cl_2$ (350 mL) at −78° C. was added $BF_3 \cdot OEt_2$ (2.0 mL, 16 mmol). After 7 min the reaction was quenched by addition of TEA (4.1 mL, 29 mmol). The resulting solution was concentrated in vacuo, dissolved in $CH_2Cl_2$, and washed with water then brine. The organic phase was dried ($MgSO_4$) and concentrated in vacuo. Final purification by column chromatography (1:1 hexanes/ethyl acetate) afforded desired tricyclic ether 121 (583 mg, 69%) as a yellow oil: $[\alpha]^{26.4}_D$=+122° (c 1.3, $CH_3OH$, 92% ee by HPLC); $^1$H NMR (CDCl$_3$) δ 6.69 (s, 1H), 6.67 (s, 1H), 4.33 (s, 2H), 3.83 (s, 3H), 3.38 (s, 3H), 3.38-3.33 (m, 1H), 2.70-2.67 (m, 2H), 2.13-2.04 (m, 1H), 1.87-1.76 (m, 3H), 1.68-1.57 (m, 2H), 1.24 (s, 3H), 1.06 (s, 3H), 0.85 (s, 3H); $^{13}$C NMR (CDCl$_3$) δ 148.7, 142.1, 129.0, 122.3, 121.3, 109.0, 77.8, 76.7, 74.9, 58.0, 55.9, 46.6, 38.3, 37.6, 28.2, 27.3, 23.0, 19.7, 14.2; HRMS (ESI) m/z calcd for $C_{19}H_{28}O_4$ ($M^+$) 320.1988, found 320.1991. The MOM acetal 22 (140 mg, 17%) also was isolated from this reaction mixture: $[\alpha]^{26.4}_D$=+34.8° (c 1.56, $CH_3OH$, 92% ee by HPLC); $^1$H NMR (CDCl$_3$) δ 6.67 (s, 1H), 6.66 (s, 1H), 4.74 (d, J=6.8 Hz, 1H), 4.61 (d, J=6.9 Hz, 1H), 4.31 (s, 2H), 3.82 (s, 3H), 3.40 (s, 3H), 3.36 (s, 3H), 3.24 (dd, J=11.5, 4.2 Hz, 1H), 2.68-2.65 (m, 2H), 2.12-2.07 (m, 1H), 1.98-1.93 (m, 1H), 1.78-1.53 (m, 3H), 1.21 (s, 3H), 1.05 (s, 3H), 0.87 (s, 3H); $^{13}$C NMR (CDCl$_3$) δ 148.6, 142.0, 128.9, 122.2, 121.1, 108.9, 96.0, 83.9, 76.6, 74.8, 57.8, 55.8, 55.5, 46.8, 38.1, 37.4, 27.2, 25.1, 22.9, 19.6, 15.0; HRMS (ESI) m/z calcd for $C_{21}H_{32}O_5$ ($M^+$) 364.2250, found 364.2256.

e. Ketone 124. To a solution of tricycle 121 (119 mg, 0.28 mmol) in $CH_2Cl_2$ at room temperature was added TPAP (9 mg, 0.03 mmol) and NMO (49 mg, 0.41 mmol). After 18.5 hours the reaction mixture was diluted with ethyl acetate, filtered through celite, and concentrated in vacuo. Final purification by column chromatography (2:3 hexanes/ethyl acetate) afforded ketone 124 (117 mg, 99%) as a colorless oil: $[\alpha]^{26.4}_D$—91.8° (c 1.1, $CH_3OH$, 92% ee by HPLC); $^1$H NMR (CDCl$_3$) δ 6.72 (s, 1H), 6.70 (s, 1H), 4.34 (s, 2H), 3.85 (s, 3H), 3.39 (s, 3H), 2.81 (dd, J=16.0, 13.6 Hz, 1H), 2.73-2.63 (m, 2H), 2.48 (ddd, J=18.5, 4.7, 3.2 Hz, 1H), 2.37 (ddd, J=13.1, 5.7, 3.2 Hz, 1H), 2.16 (dd, J=14.4, 4.7 Hz, 1H), 2.07 (dd, J=13.0, 4.9 Hz, 1H), 1.43 (s, 3H), 1.20 (s, 3H), 1.11 (s, 3H); $^{13}$C NMR (CDCl$_3$) δ 213.6, 148.8, 141.8, 129.6, 121.5, 121.0, 109.2, 75.6, 74.8, 58.0, 55.9, 47.4, 46.4, 38.0, 35.2, 24.5, 23.7, 20.8, 19.0; HRMS (ESI) m/z calcd for $C_{19}H_{26}O_4$ ($M^+$) 318.1831, found 318.1812.

f. Enone 127. To a solution of ketone 124 (152 mg, 0.48 mmol) in ethanol at room temperature was added benzaldehyde (0.2 mL, 1.7 mmol) followed by KOH (209 mg, 3.7 mmol). After 2 hours the reaction was quenched by addition of $NH_4Cl$, the resulting solution was extracted with ethyl acetate, and the combined organic extract was washed with brine. The organic phase was dried ($MgSO_4$) and concentrated in vacuo. Final purification of the residue by column chromatography (3:1 hexanes/ethyl acetate) afforded enone 127 (194 mg, 100%) as colorless oil: $[\alpha]^{26.4}_D$=201° (c 1.0, CHCl$_3$, 92% ee by HPLC); $^1$H NMR (CDCl$_3$) δ 7.63 (d, J=3.2 Hz, 1H), 7.45-7.33 (m, 5H), 6.74 (d, J=1.2 Hz, 1H), 6.71 (m, 1H), 4.35 (s, 2H), 3.39 (s, 3H), 3.55 (d, J=15.6 Hz, 1H), 3.39 (s, 3H), 3.00 (dd, J=15.6, 2.8 Hz, 1H), 2.81-2.71 (m, 2H), 2.35 (dd, J=12.4, 5.2 Hz, 1H), 1.32 (s, 3H), 1.21 (s, 3H), 1.17 (s, 3H); $^{13}$C NMR (CDCl$_3$) δ 205.0, 148.5, 141.5, 138.6, 135.0, 132.3, 130.0 (2C), 129.5, 128.6, 128.3 (2C), 121.2, 120.8, 109.3, 75.4, 74.6, 57.8, 55.9, 45.9, 45.3, 41.7, 28.7, 24.2, 22.3, 19.0; HRMS (ESI) m/z calcd for $C_{26}H_{30}O_4$ ($M^+$) 406.2144, found 406.2135.

g. Alcohol 129. To a solution of ketone 127 (1.75 g, 4.3 mmol) in $CH_3OH$ at room temperature was added $CeCl_3 \cdot 7H_2O$ (1.81 g, 4.9 mmol) followed by $NaBH_4$ (300 mg, 7.9 mmol). After 20 min, the reaction was quenched by addition of water and concentrated in vacuo. The resulting solution was extracted with ethyl acetate, and the combined extracts were washed with brine, dried ($MgSO_4$), and concentrated in vacuo, to afford alcohol 129 (1.75 g, 100%) as white crystals. This material was used in the next step without further purification: $[\alpha]^{26.4}_D$=45.3° (c 1.0, CHCl$_3$, 92% ee by HPLC); $^1$H NMR (CDCl$_3$) δ 7.33-7.21 (m, 5H), 6.77 (s, 1H), 6.68-6.67 (m, 2H), 4.32 (s, 2H), 3.91 (s, 1H), 3.81 (s, 3H), 3.39 (s, 3H), 3.36 (d, J=7.2 Hz, 1H), 2.72-2.60 (m, 2H), 2.29 (d, J=12.8 Hz, 1H), 1.90 (dd, J=11.6, 5.6 Hz, 1H), 1.19 (s, 3H), 1.04 (s, 3H), 0.83 (s, 3H); $^{13}$C NMR (CDCl$_3$) δ 148.7, 142.2, 138.2, 137.4, 129.2, 128.8 (2C), 128.2 (2C), 126.4, 124.0; 122.2, 121.3, 109.1, 80.0, 78.1, 74.9, 58.0; 55.9; 47.2; 41.2; 39.7; 27.3; 23.2; 19.8; 14.2; HRMS (ESI) m/z calcd for $C_{26}H_{32}O_4$ ($M^+$) 408.2301, found 408.2295.

h. Arene 130. To a solution of alcohol 129 (236 mg, 0.58 mmol) in $CH_2Cl_2$ at room temperature was added DIPEA (0.4 mL, 2.3 mmol) followed by MOMCl (0.1 mL, 1.3 mmol). After 15 hours, the reaction was quenched by addition of water. The resulting solution was extracted with $CH_2Cl_2$, and the combined organic phases were washed with 1N HCl followed by brine. The organic phase was dried ($MgSO_4$) and concentrated in vacuo. Final purification by column chromatography (4:1 hexanes/ethyl acetate) afforded recovered starting material (42 mg, 18%) and the MOM acetal 130 (262 mg, 68%) as a colorless oil: $[\alpha]^{264}_D$=21.7° (c 1.1, CHCl$_3$, 92% ee by HPLC); $^1$H NMR (CDCl$_3$) δ 7.34-7.19 (m, 5H), 6.68-6.67 (m, 3H), 4.78 (d, J=6.8 Hz, 1H), 4.70 (d, J=7.2 Hz, 1H), 4.33 (s, 2H), 3.99 (d, J=1.2 Hz, 1H), 3.82 (s, 3H), 3.45 (s, 3H), 3.40 (d, J=10.8 Hz, 1H), 3.38 (s, 3H), 2.73-2.67 (m, 2H), 2.29 (d, J=12.4 Hz, 1H), 1.95 (dd, J=12.4, 5.6 Hz, 1H), 1.21 (s, 3H), 1.01 (s, 3H), 0.88 (s, 3H); $^{13}$C NMR (CDCl$_3$) δ 148.7, 142.2, 137.3, 135.1, 129.3, 128.8 (2C), 128.2 (2C), 126.4, 124.9, 122.3, 121.2, 109.0; 96.2, 85.6, 78.2, 74.8, 58.0, 56.4, 55.9, 47.4, 41.4, 39.6, 27.3, 23.2, 19.6, 15.0; HRMS (ESI) m/z calcd for $C_{28}H_{36}O_5$ ($M^+$) 452.2563, found 452.2561.

i. Ketone 131. To a solution of compound 130 (35 mg, 0.08 mmol) in acetone was added $NaHCO_3$ (14 mg, 0.17 mmol)

followed by KMnO$_4$ (23 mg, 0.15 mmol). After 20 hours at rt, additional NaHCO$_3$ (70 mg, 0.83 mmol) and KMnO$_4$ (20 mg, 0.13 mmol) was added. After an additional 24 hours at rt, the reaction mixture was filtered through celite, washed with acetone, and concentrated in vacuo. Final purification by column chromatography (3:1 hexanes/ethyl acetate) afforded recovered starting material (8 mg, 23%) and ketone 131 (19 mg, 65%) as a colorless oil: $^1$H NMR (CDCl$_3$) δ 6.73 (s, 1H), 6.71 (s, 1H), 4.73 (d, J=7.2 Hz, 1H), 4.70 (d, J=7.2 Hz, 1H), 4.36 (s, 2H), 4.14 (s, 1H), 3.86 (s, 3H), 3.44 (s, 3H), 3.40 (s, 3H), 3.00-2.78 (m, 4H), 2.34 (dd, J=12.4, 5.6 Hz, 1H), 1.26 (s, 3H), 1.21 (s, 3H), 0.88 (s, 3H); $^{13}$C NMR (CDCl$_3$) δ 206.4, 150.0, 142.8, 131.2, 122.9, 122.2, 110.5, 97.4, 87.4, 79.6, 75.9, 59.2, 57.8, 57.4, 55.0, 48.4, 42.0, 28.3, 24.4, 21.8, 16.8; HRMS (ESI) m/z calcd for C$_{21}$H$_{30}$O$_6$ (M$^+$) 378.2049, found 378.2042.

j. Alcohol 133. To a solution of ketone 131 (18 mg, 0.05 mmol) in CH$_3$OH at room temperature was added NaBH$_4$ (24 mg, 0.66 mmol). After 10 min, the reaction was quenched by addition of water and concentrated in vacuo. The resulting solution was extracted with ethyl acetate, and the combined organic phases were washed with brine, dried (MgSO$_4$), and concentrated in vacuo. This afforded alcohol 133 (18 mg, 100%) as white solid, which was used in the subsequent step without further purification: [α]$^{26.4}_D$=22.2° (c 1.1, CH$_3$OH, 92% ee by HPLC); $^1$H NMR (CDCl$_3$) δ 6.70 (s, 1H), 6.68 (s, 1H), 4.82 (d, J=6.4 Hz, 1H), 4.70 (d, J=7.2 Hz, 1H), 4.34 (s, 2H), 4.31 (ddd, J=3.2, 3.2, 3.2 Hz, 1H), 3.85 (s, 3H), 3.45 (s, 3H), 3.38 (s, 3H), 3.26 (d, J=3.2 Hz, 1H), 2.77-2.60 (m, 2H), 2.54 (dd, J=14.0, 3.6 Hz, 1H), 2.36 (bd, 1H), 1.96 (dd, J=14.4, 3.6 Hz, 1H), 1.77 (dd, J=12.8, 5.2 Hz, 1H), 1.45 (s, 3H), 1.10 (s, 3H), 1.04 (s, 3H); $^{13}$C NMR (CDCl$_3$) δ 148.9, 141.8, 129.1, 122.6, 121.2, 109.2, 96.9, 84.9, 76.2, 74.9, 68.7, 57.9, 56.1, 56.0, 47.1, 42.3, 37.8, 28.7, 22.9, 21.4, 16.6; HRMS (ESI) m/z calcd for C$_{21}$H$_{32}$O$_6$ (M$^+$) 380.2199, found 380.2183.

Example 3

Synthesis of Compound 219

To a solution of protected stilbene 218 (20 mg, 0.028 mmol) in MeOH (8 mL) was added pTsOH (30 mg, 0.17 mmol). The resulting solution was stirred at room temperature for 6 hours. The reaction was quenched by addition of sat. NaHCO$_3$, extracted with ethyl acetate, and the organic phase was washed with brine and dried (MgSO$_4$). Concentration in vacuo, followed by final purification by column chromatography (2:1 to 1:1 hexanes:ethyl acetate) afforded the bis-stilbene 219 (12 mg, 78%) as a slightly yellow oil: $^1$H NMR (acetone-d6) δ 8.20 (d, J=8.7 Hz, 2H), 7.88 (s, 2H), 7.40 (d, J=8.7 Hz, 2H), 7.05-6.78 (m, 6H), 3.78 (s, 3H), 3.40-3.35 (m, 1H), 2.71-2.68 (m, 2H), 1.82-1.58 (m, 6H), 1.18 (s, 3H), 1.09 (s, 3H), 0.87 (s, 3H); $^{13}$C NMR (acetone-d6) δ 158.6 (2C), 150.0, 147.7, 146.7, 144.1, 140.2, 130.5, 129.5, 128.5, 127.2 (2C), 126.7, 126.3, 124.7 (2C), 123.6, 121.9, 111.7, 108.2, 105.9 (2C), 77.7, 77.5, 56.0, 55.4, 47.7, 39.0, 38.6, 27.8, 23.7, 20.3, 14.8; HRMS (EI) calcd for C$_{33}$H$_{35}$O$_7$N (M$^+$) 557.2414 found 557.2422.

The intermediate protected stilbene 218 was prepared as follows a. Protected Stilbene 214. A suspension of NaH (109 mg, 2.6 mmol, 60% in oil), and 15-crown-5 (1 drop, cat.) in THF (10 mL) was cooled to 0° C. To this was added aldehyde 212 (245 mg, 0.66 mmol) and the known phosphonate 213 (181 mg, 0.66 mmol) in THF (1.5 mL). After the mixture was allowed to stir for 45 mins, water was added dropwise and the solution was extracted with EtOAc. The resulting organic phase was washed with brine, dried (MgSO$_4$), and concentrated in vacuo. Final purification by column chromatography (2:1 hexanes:ethyl acetate) gave the stilbene 214 (197 mg, 61%) as a bright yellow oil: $^1$H NMR (CDCl$_3$) δ 8.21-8.18 (m, 2H), 7.65-7.62 (m, 4H), 6.88 (s, 2H), 5.30 (s, 4H), 4.74 (s, 2H), 3.53 (s, 6H), 0.98 (s, 9H), 0.13 (s, 6H); $^{13}$C NMR (CDCl$_3$) δ 156.4 (2C), 146.1, 145.9, 143.8, 129.5, 126.4 (2C), 124.7, 123.9 (2C), 113.9, 105.6 (2C), 94.7 (2C), 64.5, 56.1 (2C), 25.7 (3C), 18.2, −5.4 (2C); HRMS (EI) calcd for C$_{25}$H$_{35}$O$_7$NSi (M$^+$) 489.2183 found 489.2173.

b. Benzylic alcohol 215. Silyl ether 214 (155 mg, 0.32 mmol) was dissolved in THF (10 mL) and the solution was cooled to 0° C. To this solution was added TBAF (0.4 mL, 1.00 M in THF), and after 4 h the reaction was quenched by addition of sat. NH$_4$Cl. After extraction with ethyl acetate, the combined organic extracts were washed with water and brine, dried (MgSO$_4$), and concentrated in vacuo to give the desired benzylic alcohol 215 (120 mg, 100%) as a clear oil. $^1$H NMR (acetone-d6) δ 8.25-8.21 (m, 2H), 7.80-7.77 (m, 4H), 6.92 (s, 2H), 5.35 (s, 4H), 4.66 (d, J=5.4 Hz, 2H), 4.43 (t, J=5.4 Hz, 1H), 3.51 (s, 6H), 2.93 (s, 3H); $^{13}$C NMR (acetone-d6) δ157.2 (2C), 146.9, 145.5, 130.0, 127.2 (2C), 125.3, 124.5 (2C), 114.4, 106.6 (2C), 100.5, 95.1 (2C), 64.1, 56.2 (2C); HRMS (EI) calcd for C$_{19}$H$_{21}$O$_7$N (M$^+$) 375.1318 found 375.1315.

c. Phosphonate 216. Methanesulfonyl chloride (0.04 mL, 0.52 mmol) was added to a solution of benzylic alcohol 215 (120 mg, 0.32 mmol) and Et$_3$N (0.2 mL 1.4 mmol) in THF (10 mL) at 0° C. The reaction mixture was allowed to warm to room temperature over 1 hour, quenched by addition of H$_2$O, and extracted with EtOAc. The combined organic layers were washed with NH$_4$Cl (sat), brine, dried (MgSO$_4$), and concentrated in vacuo. The resulting residue and NaI (119 mg, 0.80 mmol) were stirred in acetone (10 mL) for 8 h. The reaction mixture was concentrated in vacuo to afford a red solid, which was dissolved in EtOAc. After the resulting yellow solution was washed with Na$_2$S$_2$O$_3$ until the color faded, it was washed with brine, dried (MgSO$_4$) and concentrated in vacuo. The resulting yellow oil was added to triethyl phosphite (2 mL) and toluene (2 mL) the reaction mixture was heated at 110° C. for 24 h. After the solution was allowed to cool to rt, the excess phosphite was removed at high vacuum. The initial orange/red oil was purified by flash chromatography (1:2 hexanes:EtOAc to 100% EtOAc) to afford phosphonate 216 (99 mg, 88%) as an orange oil: $^1$H NMR (CDCl$_3$) δ 8.21-8.18 (m, 2H), 7.64-7.61 (m, 4H), 6.81-6.80 (m, 2H), 5.28 (s, 4H), 4.07 (m, 4H), 3.52 (s, 6H), 3.13 (d, J$_{HP}$=22 Hz, 2H), 1.29 (t, J=7.0 Hz, 6H); $^{13}$C NMR (CDCl$_3$) δ 156.4 (d, J$_{CP}$=3.9 Hz, 2C), 146.4, 145.8, 133.6 (d, J$_{CP}$=9.2 Hz), 129.7, 126.6 (2C), 124.4, 124.0 (2C), 114.2 (d, J$_{CP}$=3.6 Hz), 109.9 (d, J$_{CP}$=6.2 Hz, 2C), 94.7 (2C), 62.2 (d, J$_{CP}$=6.7 Hz, 2C), 56.4 (2C), 34.0 (d, J$_{CP}$=37 Hz), 16.4 (d, J$_{CP}$=6.3 Hz, 2C); $^{31}$P NMR (CDCl$_3$) δ26.3.

d. Protected Nitro-stilbene 218. A suspension of NaH (60 mg, 1.5 mmol, 60% in oil), and 15-crown-5 (1 drop, cat.) in THF (5 mL) was cooled to 0° C. To this mixture was added a solution of aldehyde 7 (17 mg, 0.06 mmol) and phosphonate 215 (28 mg, 0.06 mmol) in THF (1 mL). The resulting mixture was allowed to warm to room temperature and stirred a total of 6 hours. After water was added dropwise, the solution was extracted with EtOAc. The resulting organic phase was washed with brine, dried (MgSO$_4$), and concentrated in vacuo. Final purification by column chromatography (3:1 to 1:1 hexanes:ethyl acetate) gave the stilbene 218 (23 mg, 59%) as an orange oil: $^1$H NMR (CDCl$_3$) δ 8.21 (d, J=8.3 Hz, 2H), 7.66 (s, 2H), 7.65 (d, J=8.3 Hz, 2H), 7.07-7.01 (m, 3H), 6.93-6.87 (m, 3H), 5.35 (s, 4H), 3.92 (s, 3H), 3.57 (s, 6H), 3.48-3.43 (m, 1H), 2.75-2.72 (m, 2H), 2.20-2.13 (m, 1H), 1.92-1.82 (m, 2H), 1.76-1.60 (m, 3H), 1.28 (s, 3H), 1.12 (s, 3H), 0.91 (s, 3H); $^{13}$C NMR (CDCl$_3$) δ 156.8 (2C), 149.0, 146.3, 146.0, 143.0, 139.3, 129.9, 129.7, 128.5, 126.6 (2C), 125.7, 124.6, 124.0 (2C), 122.6, 121.0, 114.6, 106.9, 106.1 (2C), 94.8 (2C), 77.9, 77.2, 56.4 (2C), 56.0, 46.7, 38.4, 37.6, 28.1, 27.2, 23.1, 19.9, 14.3; HRMS (EI) calcd for C$_{37}$H$_{43}$O$_9$N (M$^+$) 645.2938 found 645.2952.

Example 4

Synthesis of Compound 225

To a solution of compound 224 (16 mg, 0.03 mmol), in CH$_3$OH (2.5 mL) and ethyl acetate (0.5 mL) was added TsOH.H$_2$O (32 mg, 0.16 mmol). After 24 h, the reaction was quenched by addition of NaHCO$_3$ and concentrated in vacuo. The resulting solution was extracted with ethyl acetate, and the combined organic phase was washed with brine, dried (MgSO$_4$), and concentrated in vacuo. Final purification by column chromatography (1:1 hexanes/ethyl acetate) afforded compound 225 (13 mg, 85%) as a dark orange solid: $^1$H NMR (CDCl$_3$) δ 8.20 (d, J=8.8 Hz, 2H), 7.64 (d, J=8.8 Hz, 2H), 7.61 (d, J=16.8 Hz, 1H), 7.54 (d, J=16.8 Hz, 1H), 7.01 (d, J=16.0 Hz, 1H), 6.89 (s, 1H), 6.88 (s, 1H), 6.85 (d, J=16.0 Hz, 1H), 6.65 (s, 1H), 6.63 (s, 1H), 5.50 (brd, 1H), 3.97 (s, 3H), 3.91 (s, 3H), 3.46-3.44 (m, 1H), 2.75-2.72 (m, 2H), 2.17-2.14 (m, 2H), 1.90-1.69 (m, 4H), 1.27 (s, 3H), 1.11 (s, 3H), 0.90 (s, 3H); $^{13}$C NMR (CDCl$_3$) δ 159.2, 155.0, 149.0, 146.3, 145.5, 143.1, 139.1, 129.9, 129.2, 128.4, 126.6 (2C), 125.4, 124.8 124.0 (2C), 122.7, 120.9, 111.8, 106.9, 106.5, 101.5, 78.0, 77.7, 56.0, 55.8, 46.7, 38.4, 37.6, 28.3, 27.3, 23.1, 19.9, 14.3; HMS (ESI) m/z calcd for C$_{34}$H$_{37}$NO$_7$ (M$^+$) 571.2570, found 571.2567.

The intermediate compound 224 was prepared as follows.

a. Protected stilbene 224. To a solution of aldehyde 217 (80 mg, 0.26 mmol) and phosphonate 223 (100 mg, 0.25 mmol) in THF (4 mL) at room temperature was added 15-crown-5 (0.01 mL) followed by NaH (63 mg, 1.6 mmol, 60% in oil), which resulted in immediate color change, and after 75 min the reaction was quenched by addition of water. The resulting solution was extracted with ethyl acetate and the combined organic phases were washed with brine. The organic phase was dried (MgSO$_4$) and concentrated in vacuo. Final purification by column chromatography (1:1 hexanes/ethyl acetate) afforded recovered phosphonate 223 (12 mg, 12%) and compound 224 (94 mg, 71%) as an orange solid: $^1$H NMR (CDCl$_3$) δ 8.22-8.18 (m, 2H), 7.67-7.63 (m, 4H), 7.09-7.04 (m, 1H), 6.97-6.90 (m, 4H), 6.78-6.74 (m, 1H), 5.36 (s, 2H), 4.00 (s, 3H), 3.92 (s, 3H), 3.58 (s, 3H), 3.48-3.44 (m, 1H), 2.78-2.73 (m, 2H), 2.19-2.13 (m, 1H), 1.92-1.82 (m, 2H), 1.73-1.54 (m, 3H), 1.28 (s, 3H), 1.13 (s, 3H), 0.91 (s, 3H); $^{13}$C NMR (CDCl$_3$) δ 159.1, 156.8, 149.0, 146.2, 146.1, 143.0, 139.1, 129.8, 129.4, 128.4, 126.5 (2C), 125.8, 124.6, 124.0 (2C), 122.7, 120.9, 113.8, 106.9, 105.4, 102.4, 94.8, 77.9, 77.2, 56.4, 56.0, 55.8, 46.7, 38.4, 37.6, 28.2, 27.3, 23.1, 19.8, 14.3; HRMS (EI) calcd for C$_{36}$H$_{41}$NO$_8$ (M$^+$) 615.2832, found 615.2837.

The intermediate compound 223 was prepared as follows.

b. Aldehyde 221. To a solution of the alcohol 220 (0.45 g, 2.3 mmol) in THF (10 mL) at 0° C. was added n-BuLi (2.8 mL, 2.0 M in hexanes) dropwise over 1 min. After 25 min, the solution was cooled to −30° C. and DMF (0.23 mL, 3.0 mmol, containing some CaH$_2$ as a drying agent) was added. The reaction was allowed to progress for an additional 1 hour, and quenched by addition of saturated aq. NH$_4$Cl. After the aqueous phase was extracted with EtOAc, the combined organic phases were washed with brine, dried (MgSO$_4$), and concentrated in vacuo to afford a yellow oil. Final purification by column chromatography (2:1 to 1:2 hexanes:EtOAc) afforded aldehyde 221 (192 mg, 37%) as a clear oil, along with recovered starting material (194 mg, 43%): $^1$H NMR (CDCl$_3$) δ 10.4 (s, 1H), 6.74 (s, 1H), 6.65 (s, 1H), 5.25 (s, 2H), 4.69 (s, 2H), 3.82 (s, 3H), 3.49 (s, 3H), 3.03 (brs, 1H); $^{13}$C NMR (CDCl$_3$) δ 189.1, 162.0, 159.9, 150.4, 113.7, 104.7, 102.5, 94.6, 64.5, 56.5, 55.9. Anal. Calcd for C$_{11}$H$_{14}$O$_5$: C, 58.40; H, 6.24. Found: C, 58.69; H, 6.32.

c. Benzyl Alcohol 222. To a solution of aldehyde 221 (128 mg, 0.57 mmol) in THF (12 mL) at room temperature was added 15-crown-5 (0.01 mL), diethyl-4-nitro-benzylphosphonate (213, 203 mg, 0.74 mmol), followed by NaH (220 mg, 5.5 mmol, 60% in oil), which resulted in the rapid appearance of a maroon color. After 8 min, the reaction was quenched by slow addition of water. The resulting solution was extracted with ethyl acetate, and the combined organic phases were washed with brine, dried (MgSO$_4$), and concentrated in vacuo. Final purification by column chromatography (6:4 hexanes/THF) afforded compound 222 (191 mg, 98%) as an orange solid: $^1$H NMR (CDCl$_3$) δ 8.20-8.18 (m, 2H), 7.64-7.61 (m, 4H), 6.80 (s, 1H), 6.69 (s, 1H), 5.29 (s, 2H), 4.70 (s, 2H), 3.94 (s, 3H), 3.53 (s, 3H); $^{13}$C NMR (CDCl$_3$) δ 159.2, 156.6, 145.9, 142.9, 129.8, 126.6 (2C), 124.5, 124.3, 124.0 (2C), 113.8, 105.5, 103.1, 94.8, 65.2, 56.4, 55.8; HRMS (EI) calcd for C$_{18}$H$_{19}$NO$_6$ (M$^+$) 345.1212 found 345.1216.

d. Phosphonate 223. To a solution of benzyl alcohol 222 (193 mg, 0.56 mmol) in THF (10 mL) at room temperature was added TEA (0.2 mL, 1.4 mmol) followed by MsCl (0.1 mL, 1.3 mmol). After 50 min, the reaction was quenched by addition of water. The resulting solution was extracted with ethyl acetate, washed with brine, dried (MgSO$_4$), and concentrated in vacuo. This material was used immediately without further purification. The residue from the above step was dissolved in anhydrous acetone (8 mL) and NaI (210 mg, 1.4 mmol) was added at room temperature in the dark. After 1 h, the reaction was quenched by addition of water, the resulting solution was extracted with ethyl acetate, and washed with brine. The organic phase was dried (MgSO$_4$) and concentrated in vacuo in the dark. This material was used immediately in the next step without further purification. The residue form the above step was dissolved in DMF (3 mL), P(OEt)$_3$ (0.4 mL, 2.3 mmol) was added, and the mixture was heated to 115° C. After 17 h, an additional portion of P(OEt)$_3$ (0.4 mL, 2.3 mmol) was added. The reaction was allowed to cool to room temperature after an additional 3.5 h and concentrated in vacuo. Final purification by column chromatography (1% MeOH, 20% hexanes, 79% ethyl acetate) afforded desired phosphonate 223 (245 mg, 95% over 3 steps) as a bright yellow oil: $^1$H NMR (CDCl$_3$) δ 8.20-8.17 (m, 2H), 7.63-7.61 (m, 4H), 6.75 (s, 1H), 6.63 (s, 1H), 5.27 (s, 2H), 4.11-4.01 (m, 4H), 3.92 (s, 3H), 3.51 (s, 3H), 3.13 (d, J$_{HP}$=22 Hz, 2H), 1.28 (t, J=7.1 Hz, 6H); $^{13}$C NMR (CDCl$_3$) δ 158.8 (d, J$_{CP}$=3.8 Hz), 156.4 (d, J$_{CP}$=3.4 Hz), 146.3, 146.0, 133.5 (d, J$_{CP}$=9.1 Hz), 129.7, 126.6 (2C), 124.5, (d, J$_{CP}$=1.8 Hz), 124.0 (2C), 123.0, 109.1 (d, J$_{CP}$=7.1 Hz), 106.5 (d, J$_{CP}$=6.6 Hz), 94.9, 62.2, 62.1, 56.1 (d, J$_{CP}$=34 Hz, 2C), 34.5 (d, $J_{CP}$=138 Hz), 16.4 (d, $J_{CP}$=6.0 Hz, 2C); $^{31}$P NMR (CDCl$_3$) δ26.3; HRMS (ET) calcd for C$_{22}$H$_{28}$NO$_8$P (M$^+$) 465.1553 found 465.1552.

Example 5

Synthesis of Compound 227

To a solution of amine 226 (22 mg, 0.036 mmol), in CH$_3$OH (2 mL) and ethyl acetate (0.5 mL) was added TsOH.H$_2$O (43 mg, 0.13 mmol). After 23 h, the reaction was quenched by addition of NaHCO$_3$ and concentrated in vacuo. The resulting solution was extracted with ethyl acetate, and the combined organic phases were washed with brine. The organic phase was dried (MgSO$_4$) and concentrated in vacuo. This afforded schweinfurthin 226 (20 mg, 100%) without further purification as a dark orange solid: $^1$H NMR (CDCl$_3$) δ 7.33 (d, J=8.4 Hz, 2H), 7.22 (d, J=16.8 Hz, 1H), 7.12 (d, J=16.8 Hz, 1H), 6.95 (d, J=16.8 Hz, 1H), 6.87-6.81 (m, 3H), 6.67-6.65 (m, 3H), 6.59 (s, 1H), 3.89 (s, 3H), 3.88 (s, 3H), 3.41 (dd, J=11.8, 3.4 Hz, 1H), 2.71 (m, 2H), 2.14-2.10 (m, 1H), 1.87-1.83 (m, 2H), 1.71-1.58 (m, 2H), 1.24 (s, 3H), 1.09 (s, 3H), 0.87 (s, 3H); $^{13}$C NMR (CDCl$_3$) δ 159.5, 155.6, 150.0, 147.0, 143.8, 138.4, 133.3, 130.1, 129.9, 129.8, 128.7 (2C), 127.3, 123.8, 121.8, 117.9, 116.3 (2C), 114.4, 108.1, 107.7, 102.2, 79.0, 78.2, 57.1, 56.8, 47.8, 39.4, 38.7, 29.3, 28.4, 24.2, 20.9, 15.3; HMS (ESI) m/z calcd for C$_{34}$H$_{39}$NO$_5$ (M$^+$) 541.2828, found 541.2835.

The intermediate amine 226 was prepared as follows.

a. Protected amine 226. To a solution of compound 224 (33 mg, 0.05 mmol) in acetone (3 mL) was added sat. NH$_4$Cl (1 mL) followed by Zn dust (67 mg, 1.0 mmol) and the mixture was heated to reflux. After 70 min, the solution was allowed to cool and decanted into a separatory funnel. The resulting solution was extracted with ethyl acetate, and the combined organic phases were washed with brine, dried (MgSO$_4$), and concentrated in vacuo. Final purification by column chromatography (4:6 hexanes/ethyl acetate to 99:1 ethyl acetate/MeOH) afforded amine 226 (25 mg, 80%) as an orange oil: $^1$H NMR (CDCl$_3$) δ 7.51 (d, J=16.4 Hz, 1H), 7.37 (d, J=8.4 Hz, 2H), 7.27 (d, J=16.4 Hz, 1H), 7.01 (d, J=16.4 Hz, 1H), 6.92-6.88 (m, 4H), 6.76 (d, J=0.8 Hz, 1H), 6.67 (d, J=8.0 Hz, 2H), 5.30 (s, 2H), 3.94 (s, 3H), 3.90 (s, 3H), 3.54 (s, 3H), 3.42 (dd, J=11.8, 4.0 Hz, 1H), 2.72 (m, 2H), 2.16-2.11 (m, 1H), 1.88-1.81 (m, 3H), 1.73-1.60 (m, 2H), 1.25 (s, 3H), 1.10 (s, 3H), 0.89 (s, 3H); $^{13}$C NMR (CDCl$_3$) δ 158.4, 156.0, 148.9, 145.6, 142.6, 136.8, 132.4, 129.9, 128.7, 128.5, 127.5 (2C), 126.2, 122.6, 120.6, 116.3, 115.7, 115.1 (2C), 106.7, 105.9, 102.7, 94.9, 77.9, 77.0, 56.2, 55.9, 55.7, 46.7, 38.3, 37.6, 28.2, 27.3, 23.1, 19.8, 14.3; HMS (ESI) m/z calcd for C$_{36}$H$_{43}$NO$_6$ (M$^+$) 585.3090, found 585.3088.

Example 6

Synthesis of Compound 235

To a solution of aldehyde 234 (16 mg, 0.024 mmol), in CH$_3$OH (2 mL) and ethyl acetate (0.5 mL) was added TsOH.H$_2$O (60 mg, 0.32 mmol). After 24 h, the reaction was quenched by addition of NaHCO$_3$ and concentrated in vacuo. The resulting solution was extracted with ethyl acetate, and the combined organic phases were washed with brine. The organic phase was dried (MgSO$_4$) and concentrated in vacuo.] Final purification by column chromatography (3:7 hexanes/ethyl acetate) afforded schweinfurthin 235 (10 mg, 71%) as a dark orange wax: $^1$H NMR (CDCl$_3$) δ 8.20 (d, J=8.8 Hz, 2H), 7.67-7.61 (m, 3H), 7.55 (d, J=16.4 Hz, 1H), 7.01 (d, J=16.0 Hz, 1H), 6.89 (s, 1H), 6.88 (s, 1H), 6.85 (d, J=16.0 Hz, 1H), 6.64 (s, 2H), 4.26 (ddd, J=3.2, 3.2, 3.2 Hz, 1H), 3.96 (s, 3H), 3.90 (s, 3H), 3.39 (d, J=3.6 Hz, 1H), 2.82-2.76 (m, 2H), 2.52 (dd, J=14.4, 2.8 Hz, 1H), 2.30 (dd, J=14.4, 3.2 Hz, 1H), 1.79 (dd, J=12.8, 5.2 Hz, 1H), 1.47 (s, 3H), 1.13, (s, 3H), 1.09 (s, 3H); $^{13}$C NMR (CDCl$_3$) δ 159.2, 155.3, 149.0, 146.2, 145.7, 142.6, 139.1, 129.8, 129.2, 128.4, 126.6 (2C), 125.5, 124.8, 124.0 (2C), 122.9, 120.9, 111.9, 107.0, 106.5, 101.4, 77.5, 76.8, 70.7, 56.0, 55.8, 46.8, 43.3, 38.0, 28.9, 23.0, 21.6, 16.0; HMS (ESI) m/z calcd for C$_{34}$H$_{37}$NO$_8$ (M$^+$) 587.2519, found 587.2518.

The intermediate compound 234 was prepared as follows.

a. Compound 234. To a solution of aldehyde 134 (25 mg, 0.07 mmol) and phosphonate 223 (50 mg, 0.11 mmol) in THF (4 mL) at room temperature was added 15-crown-5 (0.01 mL) followed by NaH (51 mg, 1.3 mmol, 60% in oil), which resulted in rapid color change. After 35 min, the reaction was quenched by addition of water. The resulting solution was extracted with ethyl acetate, washed with brine, dried (MgSO$_4$) and concentrated in vacuo. Final purification by column chromatography (4:6 hexanes/ethyl acetate) afforded compound 234 (36 mg, 78%) as an orange solid: $^1$H NMR (CDCl$_3$) δ 8.19 (d, J=8.8 Hz, 2H), 7.66-7.62 (m, 4H), 7.06 (d, J=16.4 Hz, 1H), 6.96 (s, 1H), 6.95-6.90 (m, 3H), 6.77 (s, 1H), 5.35 (s, 2H), 4.83 (d, J=6.8 Hz, 1H), 4.73 (d, J=6.8 Hz, 1H), 4.32 (ddd, J=3.2, 3.2, 3.2 Hz, 1H), 3.99 (s, 3H), 3.92 (s, 3H), 3.57 (s, 3H), 3.47 (s, 3H), 3.28 (d, J=3.6 Hz, 1H), 2.81-2.75 (m, 2H), 2.57 (dd, J=14.2, 3.0 Hz, 1H), 2.34 (bd, 1H), 1.98 (dd, J=14.0, 2.8 Hz, 1H), 1.80 (dd, J=12.5, 5.2 Hz, 1H), 1.49 (s, 3H), 1.12 (s, 3H), 1.10 (s, 3H); $^{13}$C NMR (CDCl$_3$) δ 159.1, 156.8, 149.0, 146.1, 146.1, 142.6, 139.1, 129.8, 129.3, 128.4, 126.5 (2C), 125.8, 124.6, 124.0 (2C), 122.8, 120.8, 113.7, 106.8, 105.3, 102.4, 96.8, 94.8, 84.7, 76.6, 68.6, 56.3, 56.1, 55.9, 55.7, 47.0, 42.2, 37.8, 28.7, 22.9, 21.5, 16.6; HMS (ESI) m/z calcd for C$_{38}$H$_{45}$NO$_{10}$ (M$^+$) 675.3043, found 675.3040.

Example 7

Synthesis of Compound 237

To a solution of compound 236 (11 mg, 0.017 mmol), in CH$_3$OH (2 mL) was added TsOH.H$_2$O (25 mg, 0.13 mmol). After 48 h, the reaction was quenched by addition of NaHCO$_3$ and concentrated in vacuo. The resulting solution was extracted with ethyl acetate, and the combined organic phases were washed with brine. The organic phase was dried (MgSO$_4$) and concentrated in vacuo.] Final purification by column chromatography (ethyl acetate) afforded schweinfurthin 237 (9 mg, 95%) as a dark orange wax: $^1$H NMR (MeOD) δ 7.50 (d, J=16.4 Hz, 1H), 7.25 (d, J=8.4 Hz, 2H), 7.24 (d, J=16.4 Hz, 1H), 7.01-6.88 (m, 4H), 6.69 (d, J=8.4 Hz, 2H), 6.66 (d, J=1.2 Hz, 1H), 6.64 (s, 1H), 4.14 (ddd, J=3.6, 3.6, 3.6 Hz, 1H), 3.91 (s, 3H), 3.85 (s, 3H), 3.30 (obscured by solvent, 1H), 2.78-2.76 (m, 2H), 2.35 (dd, J=13.8, 3.0 Hz, 1H), 1.92 (dd, J=13.4, 3.0 Hz, 1H), 1.73 (dd, J=11.8, 6.2 Hz, 1H), 1.41 (s, 3H), 1.10 (s, 3H), 1.09 (s, 3H); $^{13}$C NMR (MeOD) δ 160.1, 157.4, 150.3, 147.9, 143.6, 138.3, 131.3, 130.6, 129.5, 128.1 (2C), 127.4, 124.4, 122.0, 117.5, 116.7 (2C), 115.8, 114.6, 108.5, 107.5, 101.9 78.8, 78.1, 71.8, 56.5, 56.2, 48 (obscured by solvent), 44.8, 39.2, 29.4, 24.0, 22.0, 16.6; HMS (ESI) m/z calcd for C$_{34}$H$_{39}$NO$_6$ (M$^+$) 557.2777, found 557.2784.

The intermediate compound 236 was prepared as follows.

a. Amine 236. To a solution of nitro compound 235 (16 mg, 0.024 mmol) in acetone (2 mL) was added sat. NH$_4$Cl (1 mL) followed by Zn dust (26 mg, 0.4 mmol) and the mixture was heated to reflux. After 80 min, the solution was cooled and decanted into a separatory funnel. The resulting solution was extracted with ethyl acetate, and the combined organic phases were washed with brine. The organic phase was dried (MgSO$_4$) and concentrated in vacuo.] Final purification by column chromatography (4:6 hexanes/ethyl acetate to 99:1 ethyl acetate/MeOH) afforded amine 236 (12 mg, 80%) as an orange oil: $^1$H NMR (CDCl$_3$) δ 7.52 (d, J=16.8 Hz, 1H), 7.37 (d, J=8.4 Hz, 2H), 7.28 (d, J=16.0 Hz, 1H), 7.01 (d, J=16.0 Hz, 1H), 6.93-6.88 (m, 4H), 6.76 (s, 1H), 6.70 (d, 8.0 Hz, 2H), 5.30 (s, 2H), 4.84 (d, J=6.8 Hz, 1H), 4.73 (d, J=6.8 Hz, 1H), 4.32 (ddd, J=2.8, 2.8, 2.8 Hz, 1H), 3.95 (s, 3H), 3.91 (s, 3H), 3.55 (s, 3H), 3.47 (s, 3H), 3.28 (d, J=2.8 Hz, 1H), 2.84-2.71 (m, 2H), 2.57 (dd, J=13.6, 2.4 Hz, 1H), 1.98 (dd, J=11.2, 2.6 Hz, 1H), 1.80 (dd, J=12.6, 5.0 Hz, 1H), 1.49 (s, 3H), 1.12 (s, 3H), 1.10 (s, 3H); $^{13}$C NMR (CDCl$_3$) δ 158.5, 156.1, 149.1, 145.2, 142.5, 136.9, 132.4, 130.4, 128.8, 128.7, 127.6 (2C), 126.3, 122.8, 120.6, 116.6, 115.8, 115.5 (2C), 107.0, 106.0, 102.8, 96.9, 95.0, 84.9, 76.5, 68.7, 56.3, 56.1, 56.0, 55.8, 47.2, 42.3, 37.9, 28.8, 23.0, 21.6, 16.7; HMS (ESI) m/z calcd for C$_{38}$H$_{47}$NO$_8$ (M$^+$) 645.3302, found 645.3312.

Example 8

Using Procedures Similar to those Described Herein, the Following Compounds of Formula (I) were also Prepared

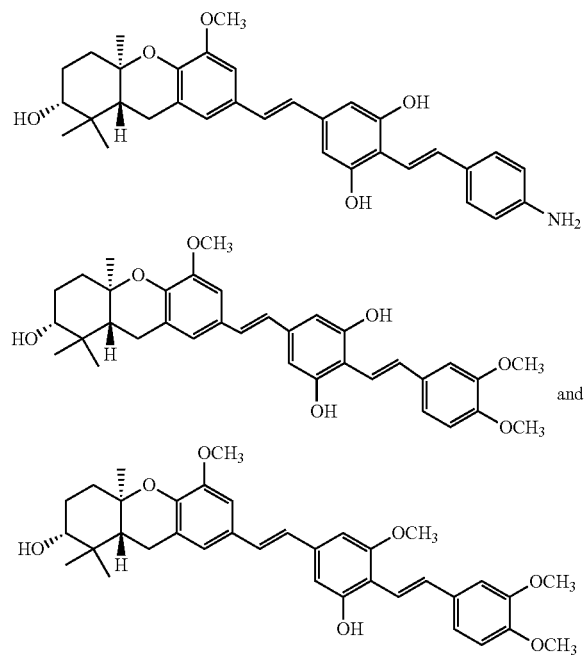

Example 9

The following illustrate representative pharmaceutical dosage forms, containing a compound of formula (I) ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 m(1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

Comparative Example 1

Synthesis of Compound 229

To a solution of 3,4-dimethoxybenzaldehyde (28, 50 mg, 0.26 mmol) and phosphonate 223 (100 mg, 0.25 mmol) in THF (4 mL) at room temperature was added 15-crown-5 (0.01 mL) followed by NaH (57 mg, 1.4 mmol, 60% in oil), which resulted in immediate color change, and after 65 min the reaction was quenched by addition of water. The resulting solution was extracted with ethyl acetate, and the combined organic phases were washed with brine. The organic phase was dried (MgSO$_4$) and concentrated in vacuo.] Final purification by column chromatography (3:1 hexanes/ethyl acetate to ethyl acetate) afforded recovered phosphonate 223 (27 mg, 27%) and compound 229 (94 mg, 71%) as an orange solid: $^1$H NMR (CDCl$_3$) δ 8.19 (d, J=8.8 Hz, 2H), 7.66 (s, 2H), 7.63 (d, J=8.8 Hz, 2H), 7.11-7.07 (m, 3H), 6.96 (s, 1H), 6.96 (s, 1H), 6.87 (d, J=8.0 Hz, 1H), 6.78 (s, 1H), 5.34 (s, 2H), 3.99 (s, 3H), 3.96 (s, 3H), 3.91 (s, 3H), 3.56 (s, 3H); $^{13}$C NMR (CDCl$_3$) δ 159.1, 156.8, 149.1, 149.0, 146.1, 146.1, 138.9, 129.9, 129.5, 129.5, 126.6 (2C), 126.3, 124.6, 124.0 (2C), 120.2, 113.9, 111.1, 108.5, 105.4, 102.4, 94.8, 56.4, 55.9, 55.8, 55.7; HMS (ESI) m/z calcd for C$_{27}$H$_{27}$NO$_7$ (M$^+$) 477.1788, found 477.1771.

Comparative Example 2

Synthesis of Compound 230

To a solution of compound 229 (20 mg, 0.042 mmol), in CH$_3$OH (4 mL) and ethyl acetate (2 mL) was added TsOH.H$_2$O (54 mg, 0.28 mmol). After 18.5 h, the reaction was quenched by addition of NaHCO$_3$ and concentrated in vacuo. The resulting solution was extracted with ethyl acetate, and the combined organic phases were washed with brine. The organic phase was dried (MgSO$_4$) and concentrated in vacuo. Final purification by column chromatography (6:4 hexanes/ethyl acetate to 4:6 hexanes/ethyl acetate) afforded compound 230 (16 mg, 88%) as a dark orange solid: $^1$H NMR (D$_6$-Acetone) δ 8.22 (d, J=9.2 Hz, 2H), 7.81 (s, 2H), 7.76 (d, J=9.2 Hz, 2H), 7.25 (d, J=2.0 Hz, 1H), 7.19 (d, J=16.0 Hz, 1H), 7.00 (dd, J=8.4, 2.0 Hz, 1H), 7.04 (d, J=16.4 Hz, 1H), 6.95 (d, J=8.4 Hz, 1H), 6.85 (d, J=1.2 Hz, 1H), 6.81 (d, J=1.2 Hz, 1H), 4.00 (s, 3H), 3.87 (s, 3H), 3.83 (3H); $^{13}$C NMR (D$_6$-Acetone) δ 160.5, 158.1, 150.7, 150.6, 147.4, 147.1, 140.3, 131.2, 130.3, 129.3, 127.4 (2C), 127.1, 126.0, 124.8 (2C), 121.1, 112.7, 110.4, 107.6, 104.5, 101.5, 56.2, 56.1, 56.1; HMS (ESI) m/z calcd for C$_{25}$H$_{23}$NO$_6$ (M$^+$) 433.1525, found 433.1522.

Comparative Example 3

Synthesis of Compound 231

To a solution of compound 229 (20 mg, 0.04 mmol) in acetone (4 mL) was added sat. NH$_4$Cl (1 mL) followed by Zn dust (30 mg, 0.46 mmol) and the mixture was heated to reflux. After 90 min, the solution was cooled and decanted into a separatory funnel. The resulting solution was extracted with ethyl acetate, and the combined organic phases were washed with brine. The organic phase was dried (MgSO$_4$) and concentrated in vacuo. Final purification by column chromatography (4:6 hexanes/ethyl acetate) afforded amine 231 (12 mg, 67%) as orange solid: $^1$H NMR (CDCl$_3$) δ 7.53 (d, J=16.8 Hz, 1H), 7.37 (d, J=8.8 Hz, 2H), 7.28 (d, J=16.8 Hz, 1H), 7.09 (d, J=2.0 Hz, 1H), 7.06 (dd, J=8.4, 2.0 Hz, 1H), 7.04 (d, J=16.4 Hz, 1H), 6.94 (d, J=1.2 Hz, 1H), 6.93 (d, J=16.4 Hz, 1H), 6.87 (d, J=8.4 Hz, 1H), 6.77 (d, J=0.8 Hz, 1H), 6.68 (d, J=8.4 Hz, 2H), 5.31 (s, 2H), 3.96 (s, 3H), 3.95 (s, 3H), 3.91 (s, 3H), 3.55 (s, 3H); $^{13}$C NMR (CDCl$_3$) δ 158.4, 156.0, 149.0, 148.9, 145.7, 136.6, 132.5, 130.3, 129.9, 128.3, 127.6 (2C), 126.8, 119.9, 116.3, 115.8, 115.2 (2C), 111.1, 108.5, 106.0, 102.7, 94.9, 56.3, 55.9, 55.8, 55.7; HMS (ESI) m/z calcd for C$_{27}$H$_{29}$NO$_5$ (M$^+$) 447.0246, found 447.2051.

Comparative Example 4

Synthesis of Compound 232

To a solution of compound 231 (10 mg, 0.02 mmol), in CH$_3$OH (1 mL) and ethyl acetate (0.5 mL) was added TsOH.H$_2$O (60 mg, 0.31 mmol). After 18.5 h, the reaction was quenched by addition of NaHCO$_3$ and concentrated in vacuo. The resulting solution was extracted with ethyl acetate, and the combined organic phases were washed with brine. The organic phase was dried (MgSO$_4$) and concentrated in vacuo. Final purification by column chromatography (4:6 hexanes/ethyl acetate) afforded compound 232 (8 mg, 89%) as a dark orange solid: $^1$H NMR (D$_6$-Acetone) δ 7.56 (d, J=16.8 Hz, 1H), 7.29-7.22 (m, 3H), 7.10-6.92 (m, 6H), 6.76 (d, J=2.8 Hz, 1H), 6.65 (d, J=8.4 Hz, 2H), 4.69 (brd, 1H), 3.92 (s, 3H), 3.85 (s, 3H), 3.81 (s, 3H); $^{13}$C NMR (D$_6$-Acetone) δ 159.6, 156.9, 150.6, 150.4, 148.7, 137.6, 132.8, 131.5, 129.3, 128.9, 128.0 (2C), 127.5, 120.8, 116.4, 115.3 (2C), 112.8, 110.3, 107.7, 104.5, 101.6, 56.1, 56.1, 56.0; HMS (ESI) m/z calcd for C$_{25}$H$_{25}$NO$_4$ (M$^+$) 403.1784, found 403.1779.

Compounds 229, 230, 231, and 232 are also compounds of the invention.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:
1. A compound of formula (I):

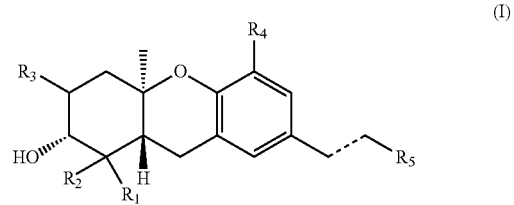

wherein:
  R$_1$ and R$_2$ are each independently H, (C$_1$-C$_6$)alkyl, halo(C$_1$-C$_6$)alkyl or (C$_3$-C$_8$)cycloalkyl; or one of R$_1$ and R$_2$ is carboxy and the other is H, (C$_1$-C$_6$)alkyl, halo(C$_1$-C$_6$)alkyl or (C$_3$-C$_8$)cycloalkyl;
  R$_3$ is H, (C$_1$-C$_{15}$)alkyl, (C$_2$-C$_{15}$)alkenyl, (C$_2$-C$_{15}$)alkynyl, (C$_1$-C$_{15}$)alkoxy, (C$_1$-C$_{15}$)alkylthio, (C$_1$-C$_{15}$)alkanoyl, (C$_1$-C$_{15}$)alkoxycarbonyl, (C$_2$-C$_{15}$)alkanoyloxy, hydroxy, mercapto, halo, cyano, or NR$^a$R$^b$;
  R$_4$ is H, hydroxy, (C$_1$-C$_{15}$)alkyl, (C$_2$-C$_{15}$)alkenyl, (C$_2$-C$_{15}$)alkynyl, (C$_1$-C$_{15}$)alkoxy, (C$_1$-C$_{15}$)alkylthio, (C$_1$-C$_{15}$)alkanoyl, $(C_1-C_{15})$alkoxycarbonyl, $(C_2-C_{15})$alkanoyloxy, halo, cyano, trifluoromethyl, trifluoromethoxy, nitro, or $NR^cR^d$;

$R_5$ is aryl or heteroaryl, which aryl or heteroaryl is substituted with one or more groups $R^x$, and which aryl or heteroaryl is also optionally substituted with one or more halo, hydroxy, cyano, trifluoromethyl, trifluoromethoxy, $NR^eR^f$, $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, $-P(=O)(OH)_2$ or $(C_2-C_{15})$alkanoyloxy;

$R^a$ and $R^b$ are each independently H, $(C_1-C_6)$alkyl, or $(C_1-C_{15})$alkanoyl;

$R^c$ and $R^d$ are each independently H, $(C_1-C_6)$alkyl, or $(C_1-C_{15})$alkanoyl;

$R^e$ and $R^f$ are each independently H, $(C_1-C_6)$alkyl, or $(C_1-C_{15})$alkanoyl; each $R^x$ is independently $R^y$ or $-CH=CH-R^y$;

each $R^y$ is independently aryl or heteroaryl, which aryl or heteroaryl is optionally substituted with one or more groups independently selected from hydroxy, $(C_1-C_6)$alkyl, $(C_2-C_6)$alkenyl, $(C_2-C_6)$alkynyl, $(C_1-C_6)$alkoxy, $(C_1-C_6)$alkylthio, $(C_1-C_6)$alkanoyl, $(C_1-C_6)$alkoxycarbonyl, $(C_2-C_6)$alkanoyloxy, halo, cyano, trifluoromethyl, trifluoromethoxy, nitro, and $NR^vR^w$; wherein each $R^v$ and $R^w$ is independently H, $(C_1-C_6)$alkyl, or $(C_1-C_{15})$alkanoyl; and the bond represented by ----- is a single or a double bond; wherein any $(C_1-C_{15})$alkyl, $(C_2-C_{15})$alkenyl, $(C_2-C_{15})$alkynyl, $(C_1-C_{15})$alkoxy, $(C_1-C_{15})$alkylthio, $(C_1-C_{15})$alkanoyl, $(C_1-C_{15})$alkoxycarbonyl, or $(C_2-C_{15})$alkanoyloxy, of $R_1-R_4$ is optionally substituted with one or more halo, hydroxy, cyano, or oxo (=O);

or a pharmaceutically acceptable salt thereof.

2. The compound of claim 1 wherein the compound of formula (I) is not the compound,

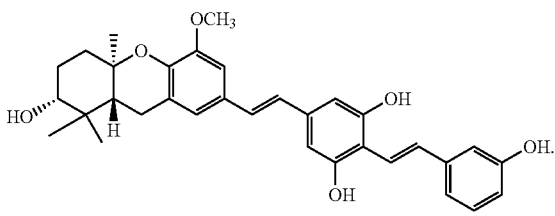 [SMILES: COc1cc(/C=C/c2cc(O)c(/C=C/c3cccc(O)c3)c(O)c2)cc2c1O[C@]1(C)CC[C@@H](O)C(C)(C)[C@H]1C2]

3. The compound of claim 1 wherein $R_1$ is $(C_1-C_6)$ alkyl.
4. The compound of claim 1 wherein $R_1$ is methyl.
5. The compound of claim 1 wherein $R_2$ is $(C_1-C_6)$ alkyl.
6. The compound of claim 1 wherein $R_2$ is methyl.
7. The compound of claim 1 wherein $R_3$ is H.
8. The compound of claim 1 wherein $R_4$ is methoxy.
9. The compound of claim 1 wherein $R_5$ is aryl that is substituted with one or two groups $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.
10. The compound of claim 1 wherein $R_5$ is aryl that is substituted with one group $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.
11. The compound of claim 1 wherein $R_5$ is phenyl that is substituted with one or two groups $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.
12. The compound of claim 1 wherein $R_5$ is phenyl that is substituted with one group $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.
13. The compound of claim 1 wherein $R_5$ is of the formula

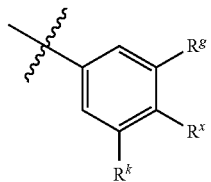

wherein:
$R^g$ and $R^k$ are each independently H, halo, hydroxy, $(C_1-C_{15})$alkyl, $(C_2-C_{15})$alkenyl, $(C_2-C_{15})$alkynyl, $(C_1-C_{15})$alkoxy, methoxymethoxy, and $(C_2-C_{15})$alkanoyloxy; wherein any $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy of $R^g$ and $R^k$ is optionally substituted with one or more halo, hydroxy, cyano, or oxo (=O).

14. The compound of claim 1 wherein $R_5$ is of the formula

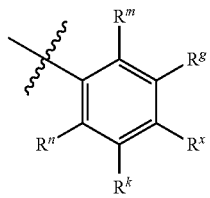

wherein:
$R^g$ and $R^k$ are each independently H, halo, hydroxy, $(C_1-C_{15})$alkyl, $(C_2-C_{15})$alkenyl, $(C_2-C_{15})$alkynyl, $(C_1-C_{15})$alkoxy, methoxymethoxy, and $(C_2-C_{15})$alkanoyloxy;
$R^m$ is H, cyano, fluoro, or $-P(=O)(OH)_2$; and
$R^n$ is H, cyano, fluoro, or $-P(=O)(OH)_2$;
wherein any $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy of $R^g$ and $R^k$ is optionally substituted with one or more halo, hydroxy, cyano, or oxo (=O).

15. The compound of claim 14 wherein $R^g$ and $R^k$ are each independently H, fluoro, chloro, bromo, hydroxy, or methoxy.
16. The compound of claim 14 wherein at least one of $R^g$ and $R^k$ is hydroxy.
17. The compound of any claim 1 wherein $R_5$ is an isoxazolyl, imidazolyl, pyridyl, indolyl, or benzo[b]furanyl ring that is substituted with one group $R^x$ and that is also optionally substituted with one or more halo, hydroxy, cyano, trifluoromethyl, trifluoromethoxy, $NR^eR^f$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy.

18. The compound of claim 1 wherein each $R^x$ is independently $R^y$.

19. The compound of claim 1 wherein each $R^x$ is independently —CH=CH—$R^y$.

20. The compound of claim 1 wherein each $R^y$ is independently aryl which is optionally substituted with one or more groups independently selected from hydroxy, $(C_1-C_6)$alkyl, $(C_2-C_6)$alkenyl, $(C_2-C_6)$alkynyl, $(C_1-C_6)$alkoxy, $(C_1-C_6)$alkylthio, $(C_1-C_6)$alkanoyl, $(C_1-C_6)$alkoxycarbonyl, $(C_2-C_6)$alkanoyloxy, halo, cyano, trifluoromethyl, trifluoromethoxy, nitro, and $NR^vR^w$; wherein each $R^v$ and $R^w$ is independently H, $(C_1-C_6)$alkyl, or $(C_1-C_{15})$alkanoyl.

21. The compound of claim 1 wherein each $R^y$ is independently heteroaryl which is optionally substituted with one or more groups independently selected from hydroxy, $(C_1-C_6)$alkyl, $(C_2-C_6)$alkenyl, $(C_2-C_6)$alkynyl, $(C_1-C_6)$alkoxy, $(C_1-C_6)$alkylthio, $(C_1-C_6)$alkanoyl, $(C_1-C_6)$alkoxycarbonyl, $(C_2-C_6)$alkanoyloxy, halo, cyano, trifluoromethyl, trifluoromethoxy, nitro, and $NR^vR^w$; wherein each $R^v$ and $R^w$ is independently H, $(C_1-C_6)$alkyl, or $(C_1-C_{15})$alkanoyl.

22. The compound of claim 1 wherein each $R^y$ is independently phenyl which is optionally substituted with one or more groups independently selected from hydroxy, $(C_1-C_6)$alkyl, $(C_2-C_6)$alkenyl, $(C_2-C_6)$alkynyl, $(C_1-C_6)$alkoxy, $(C_1-C_6)$alkylthio, $(C_1-C_6)$alkanoyl, $(C_1-C_6)$alkoxycarbonyl, $(C_2-C_6)$alkanoyloxy, halo, cyano, trifluoromethyl, trifluoromethoxy, nitro, and $NR^vR^w$; wherein each $R^v$ and $R^w$ is independently H, $(C_1-C_6)$alkyl, or $(C_1-C_{15})$alkanoyl.

23. The compound of any claim 1 wherein each $R^y$ is independently phenyl which is optionally substituted with one or more groups independently selected from hydroxy, $(C_1-C_6)$alkyl, $(C_2-C_6)$alkenyl, $(C_1-C_6)$alkoxy, $(C_1-C_6)$alkoxycarbonyl, $(C_2-C_6)$alkanoyloxy, halo, cyano, trifluoromethyl, trifluoromethoxy, nitro, and $NR^vR^w$; wherein each $R^v$ and $R^w$ is independently H, $(C_1-C_6)$alkyl, or $(C_1-C_{15})$alkanoyl.

24. The compound of claim 1 which is selected from:

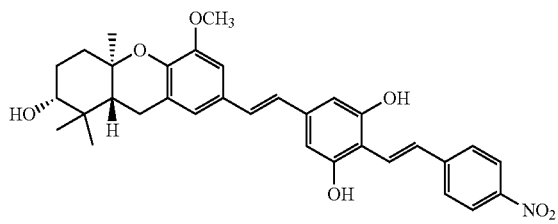

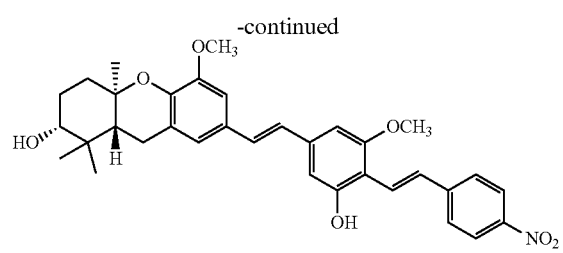

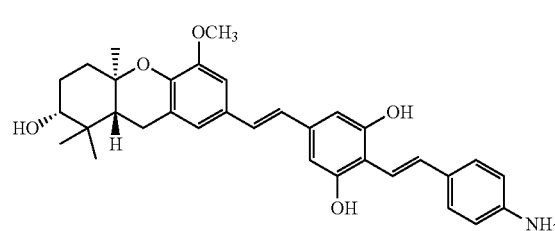

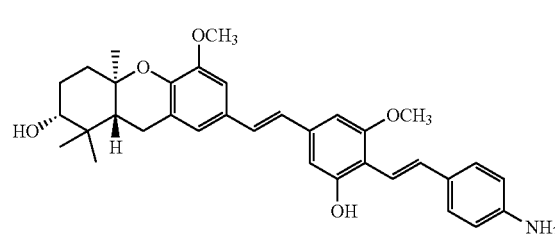

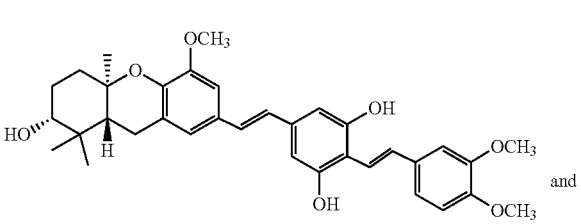

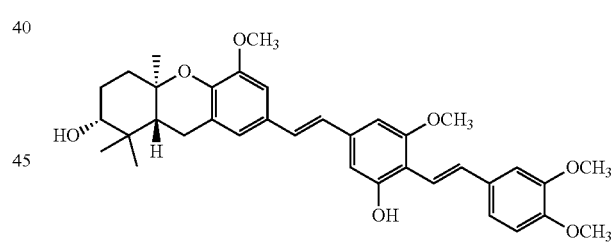

or a pharmaceutically acceptable salt thereof.

25. The compound of claim 1 which is selected from:

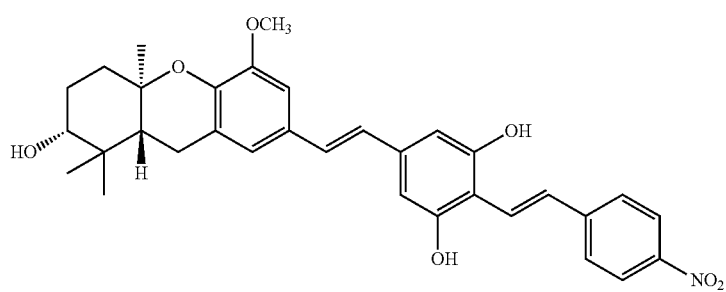

219

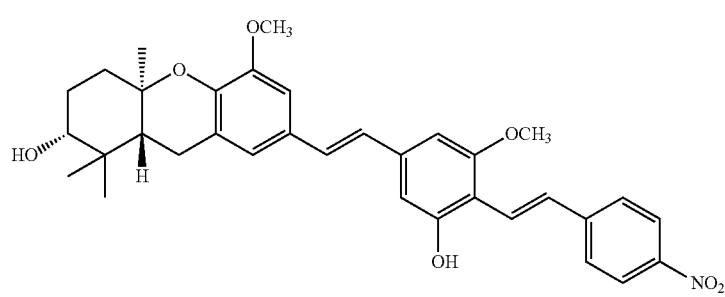

225

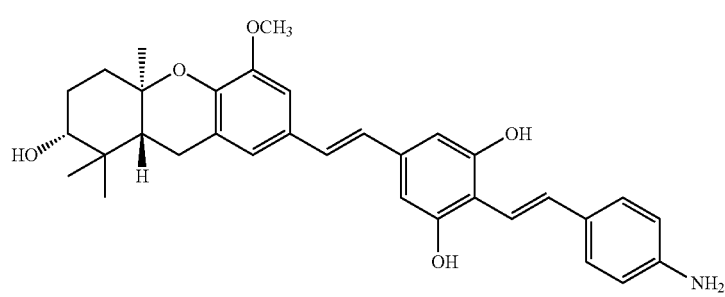

227

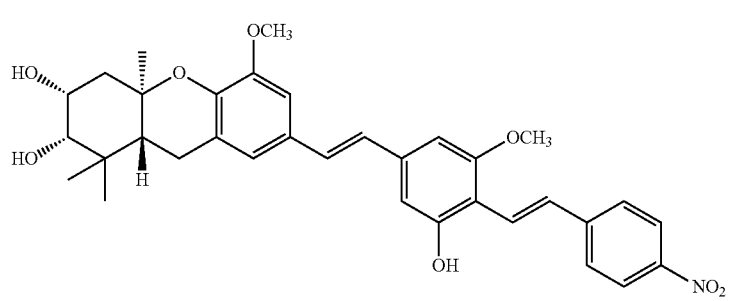

235 and

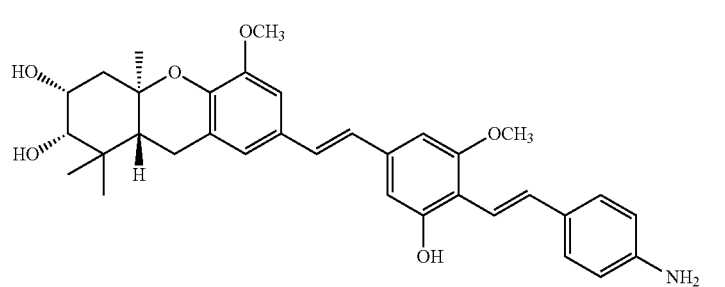

237 or a pharmaceutically acceptable salt thereof.

26. The compound as described in claim 1 which is isolated and purified.

27. A pharmaceutical composition comprising a compound as described in claim 1 and a pharmaceutically acceptable carrier.

28. A method for treating cancer comprising administering a therapeutically effective amount of a compound as described in claim 1 to a mammal.

29. The method of claim 28 wherein the cancer is breast cancer or a cancer of the CNS or renal system.

* * * * *

UNITED STATES PATENT AND TRADEMARK OFFICE
CERTIFICATE OF CORRECTION

PATENT NO. : 8,637,685 B2  Page 1 of 1
APPLICATION NO. : 13/001509
DATED : January 28, 2014
INVENTOR(S) : Wiemer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 492 days.

Signed and Sealed this
Twenty-second Day of September, 2015

Michelle K. Lee
*Director of the United States Patent and Trademark Office*

UNITED STATES PATENT AND TRADEMARK OFFICE
CERTIFICATE OF CORRECTION

| | |
|---|---|
| PATENT NO. | : 8,637,685 B2 |
| APPLICATION NO. | : 13/001509 |
| DATED | : January 28, 2014 |
| INVENTOR(S) | : Wiemer et al. |

It is certified that error appears in the above-identified patent and that said Letters Patent is hereby corrected as shown below:

In the Claims

In Claim 17, Column 46, Line 61:

Replace:

The compound of any claim 1,

With:

The compound of claim 1,

Signed and Sealed this
Twenty-ninth Day of September, 2015

Michelle K. Lee
*Director of the United States Patent and Trademark Office*